United States Patent [19]
Hostetter et al.

[11] Patent Number: 5,886,151
[45] Date of Patent: Mar. 23, 1999

[54] *CANDIDA ALBICANS* INTEGRIN-LIKE PROTEIN

[75] Inventors: Margaret K. Hostetter; Cheryl A. Gale, both of Minneapolis; Catherine M. Bendel, Hopkins, all of Minn.; Nian-jun Tao, Malden, Mass.; Kathleen Kendrick, Columbus, Ohio

[73] Assignee: Regents of the University of Minnesota, Minneapolis, Minn.

[21] Appl. No.: 642,846

[22] Filed: May 3, 1996

[51] Int. Cl.⁶ .............................. C07K 14/40; C07K 7/08; A61K 39/00
[52] U.S. Cl. ..................... 530/371; 530/300; 530/326; 424/274.1
[58] Field of Search ............................ 530/371, 326, 530/300; 424/274.1, 276.1

[56] References Cited

U.S. PATENT DOCUMENTS

| | | | |
|---|---|---|---|
| 4,542,020 | 9/1985 | Jackson et al. | 514/31 |
| 4,661,454 | 4/1987 | Botstein et al. | 435/256 |
| 4,670,382 | 6/1987 | Buckley et al. | 435/7 |
| 4,735,901 | 4/1988 | Kurtz et al. | 435/172.3 |
| 4,806,465 | 2/1989 | Buckley et al. | 435/7 |
| 4,835,098 | 5/1989 | Orr et al. | 435/6 |
| 5,139,936 | 8/1992 | Botstein et al. | 435/69.1 |
| 5,332,660 | 7/1994 | Takeda et al. | 435/6 |

*Primary Examiner*—Lila Feisee
*Assistant Examiner*—Claire M. Kaufman
*Attorney, Agent, or Firm*—Mueting, Raasch & Gebhardt, P.A.

[57] ABSTRACT

An isolated and purified DNA molecule encoding *Candida albicans* protein with integrin-like motifs, the protein itself, antibodies thereto, and methods of use, are provided.

5 Claims, 2 Drawing Sheets

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 5194 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
CCCAAAAAAG  ATAAAATAAA  AACAAAACAA  AACAAAAGTA  CTAACAAATT  ATTGAAACTT    60
TTAATTTTTA  ATAAAGAATC  AGTAGATCTA  TTGTTAAAAG  AAATGAACTC  AACTCCAAGT   120
AAATTATTAC  CGATAGATAA  ACATTCTCAT  TTACAATTAC  AGCCTCAATC  GTCCTCGGCA   180
TCAATATTTA  ATTCCCAAC   AAAACCATTG  AATTTCCCCA  GAACAAATTC  CAAGCCGAGT   240
TTAGATCCAA  ATTCAAGCTC  TGATACCTAC  ACTAGCGAAC  AAGATCAAGA  GAAAGGGAAA   300
GAAGAGAAAA  AGGACACAGC  CTTTCAAACA  TCTTTTGATA  GAAATTTTGA  TCTTGATAAT   360
TCAATCGATA  TACAACAAAC  AATTCAACAT  CAGCAACAAC  AGCCACAACA  ACAACAACAA   420
CTCTCACAAA  CCGACAATAA  TTTAATTGAT  GAATTTTCTT  TTCAAACACC  GATGACTTCG   480
ACTTTAGACC  TAACCAAGCA  AAATCCAACT  GTGGACAAAG  TGAATGAAAA  TCATGCACCA   540
ACTTATATAA  ATACCTCCCC  CAACAAATCA  ATAATGAAAA  AGGCAACTCC  TAAAGCGTCA   600
CCTAAAAAAG  TTGCATTTAC  TGTAACTAAT  CCCGAAATTC  ATCATTATCC  AGATAATAGA   660
GTCGAGGAAG  AAGATCAAAG  TCAACAAAAA  GAAGATTCAG  TTGAGCCACC  CTTAATACAA   720
CATCAATGGA  AAGATCCTTC  TCAATTCAAT  TATTCTGATG  AAGATACAAA  TGCTTCAGTT   780
CCACCAACAC  CACCACTTCA  TACGACGAAA  CCTACTTTTG  CGCAATTATT  GAACAAAAAC   840
AACGAAGTCA  ATCTGGAACC  AGAGGCATTG  ACAGATATGA  AATTAAAGCG  CGAAAATTTC   900
AGCAATTTAT  CATTAGATGA  AAAAGTCAAT  TTATATCTTA  GTCCACTAA   TAATAACAAT   960
AGTAAGAATG  TGTCAGATAT  GGATCTGCAT  TTACAAAACT  TGCAAGACGC  TTCGAAAAAC  1020
AAAACTAATG  AAAATATTCA  CAATTTGTCA  TTTGCTTTAA  AAGCACCAAA  GAATGATATT  1080
GAAAACCCAT  TAAACTCATT  GACTAACGCA  GATATTCTGT  TAAGATCATC  TGGATCATCA  1140
CAATCGTCAT  TACAATCTTT  GAGGAATGAC  AATCGTGTCT  GGAATCAGT   GCCTGGGTCA  1200
CCTAAGAAGG  TTAATCCTGG  ATTGTCTTTG  AATGACGGCA  TAAAGGGGTT  CTCTGATGAG  1260
GTTGTTGAAT  CATTACTTCC  TCGTGACTTA  TCTCGAGACA  AATTAGAGAC  TACAAAAGAA  1320
CATGATGCAC  CAGAACACAA  CAATGAGAAT  TTTATTGATG  CTAAATCGAC  TAATACCAAT  1380
AAGGGACAAC  TCTTAGTATC  ATCTGATGAT  CATTTGGACT  CTTTTGATAG  ATCCTATAAC  1440
CACACTGAAC  AATCAATTTT  GAATCTTTTG  AATAGTGCAT  CACAATCTCA  AATTTCGTTA  1500
AATGCATTGG  AAAAACAAAG  GCAAACACAG  GAACAAGAAC  AAACACAAGC  GGCAGAGCCT  1560
GAAGAAGAAA  CTTCGTTTAG  TGATAATATC  AAAGTTAAAC  AAGAGCCAAA  GAGCAATTTG  1620
GAGTTTGTCA  AGGTTACCAT  CAAGAAAGAA  CCAGTTCTGG  CCACGGAAAT  AAAAGCTCCA  1680
AAAAGAGAAT  TTTCAAGTCG  AATATTAAGA  ATAAAAAATG  AAGATGAAAT  TGCCGAACCA  1740
GCTGATATTC  ATCCTAAAAA  AGAAAATGAA  GCAAACAGTC  ATGTCGAAGA  TACTGATGCA  1800
TTGTTGAAGA  AAGCACTTAA  TGATGATGAG  GAATCTGACA  CGACCCAAAA  CTCAACGAAA  1860
ATGTCAATTC  GTTTTCATAT  TGATAGTGAT  TGGAAATTGG  AAGACAGTAA  TGATGGCGAT  1920
AGAGAAGATA  ATGATGATAT  TTCTCGTTTT  GAGAAATCAG  ATATTTTGAA  CGACGTATCA  1980
CAGACTTCTG  ATATTATTGG  TGACAAATAT  GGAAACTCAT  CAAGTGAAAT  AACCACCAAA  2040
ACATTAGCAC  CCCCAAGATC  GGACAACAAT  GACAAGGAGA  ATTCTAAATC  TTTGGAAGAT  2100
CCAGCTAATA  ATGAATCATT  GCAACAACAA  TTGGAGGTAC  CGCATACAAA  AGAAGATGAT  2160
AGCATTTTAG  CCAACTCGTC  CAATATTGCT  CCACCTGAAG  AATTGACTTT  GCCCGTAGTG  2220
GAAGCAAATG  ATTATTCATC  TTTTAATGAC  GTGACCAAAA  CTTTTGATGC  ATACTCAAGC  2280
TTTGAAGAGT  CATTATCTAG  AGAGCACGAA  ACTGATTCAA  AACCAATTAA  TTTCATATCA  2340
ATTTGGCATA  AACAAGAAAA  GCAGAAGAAA  CATCAAATTC  ATAAAGTTCC  AACTAAACAG  2400
```

-continued

| | | | | | | |
|---|---|---|---|---|---|---|
| ATCATTGCTA | GTTATCAACA | ATACAAAAAC | GAACAAGAAT | CTCGTGTTAC | TAGTGATAAA | 2460 |
| GTGAAAATCC | CAAATGCCAT | ACAATTCAAG | AAATTCAAAG | AGGTAAATGT | CATGTCAAGA | 2520 |
| AGAGTTGTTA | GTCCAGACAT | GGATGATTTG | AATGTATCTC | AATTTTTACC | AGAATTATCT | 2580 |
| GAAGACTCTG | GATTTAAAGA | TTTGAATTTT | GCCAACTACT | CCAATAACAC | CAACAGACCA | 2640 |
| AGAAGTTTTA | CTCCATTGAG | CACTAAAAAT | GTCTTGTCGA | ATATTGATAA | CGATCCTAAT | 2700 |
| GTTGTTGAAC | CTCCTGAACC | GAAATCATAT | GCTGAAATTA | GAAATGCTAG | ACGGTTATCA | 2760 |
| GCTAATAAGG | CAGCGCCAAA | TCAGGCACCA | CCATTGCCAC | CACAACGACA | ACCATCTTCA | 2820 |
| ACTCGTTCCA | ATTCAAATAA | ACGAGTGTCC | AGATTTAGAG | TGCCCACATT | TGAAATTAGA | 2880 |
| AGAACTTCTT | CAGCATTAGC | ACCTTGTGAC | ATGTATAATG | ATATTTTTGA | TGATTTCGGT | 2940 |
| GCGGGTTCTA | AACCAACTAT | AAAGGCAGAA | GGAATGAAAA | CATTGCCAAG | TATGGATAAA | 3000 |
| GATGATGTCA | AGAGGATTTT | GAATGCAAAG | AAAGGTGTGA | CTCAAGATGA | ATATATAAAT | 3060 |
| GCCAAACTTG | TTGATCAAAA | ACCTAAAAAG | AATTCAATTG | TCACCGATCC | CGAAGACCGA | 3120 |
| TATGAAGAAT | TACAACAAAC | TGCCTCTATA | CACAATGCCA | CCATTGATTC | AAGTATTTAT | 3180 |
| GGCCGACCAG | ACTCCATTTC | TACCGACATG | TTGCCTTATC | TTAGTGATGA | ATTGAAAAAA | 3240 |
| CCACCTACGG | CTTTATTATC | TGCTGATCGT | TTGTTTATGG | AACAAGAAGT | ACATCCGTTA | 3300 |
| AGATCAAACT | CTGTTTTGGT | TCACCCAGGG | GCAGGAGCAG | CAACTAATTC | TTCAATGTTA | 3360 |
| CCAGAGCCAG | ATTTTGAATT | AATCAATTCA | CCTGCTAGAA | ATGTGCTGAA | CAACAGTGAT | 3420 |
| AATGTCGCCA | TCAGTGGTAA | TGCTAGTACT | ATTAGTTTTA | ACCAATTGGA | TATGAATTTT | 3480 |
| GATGACCAAG | CTACAATTGG | TCAAAAAATC | CAAGAGCAAC | CTGCTTCAAA | ATCCGCCAAT | 3540 |
| ACTGTTCGTG | GTGATGATGA | TGGATTGGCC | AGTGCACCTG | AAACACCAAG | AACTCCTACC | 3600 |
| AAAAAGGAGT | CCATATCAAG | CAAGCCTGCC | AAGCTTTCTT | CTGCCTCCCC | TAGAAAATCA | 3660 |
| CCAATTAAGA | TTGGTTCACC | AGTTCGAGTT | ATTAAGAAAA | ATGGATCAAT | TGCTGGCATT | 3720 |
| GAACCAATCC | CAAAAGCCAC | TCACAAACCG | AAGAAATCAT | TCCAAGGAAA | CGAGATTTCA | 3780 |
| AACCATAAAG | TACGAGATGG | TGGAATTTCA | CCAAGCTCCG | GATCAGAGCA | TCAACAGCAT | 3840 |
| AATCCTAGTA | TGGTTTCTGT | TCCTTCACAG | TATACTGATG | CTACTTCAAC | GGTTCCAGAT | 3900 |
| GAAAACAAAG | ATGTTCAACA | CAAGCCTCGT | GAAAAGCAAA | AGCAAAAGCA | TCACCATCGC | 3960 |
| CATCATCATC | ATCATCATAA | ACAAAAAACT | GATATTCCGG | GTGTTGTTGA | TGATGAAATT | 4020 |
| CCTGATGTAG | GATTACAAGA | ACGAGGCAAA | TTATTCTTTA | GAGTTTTAGG | AATTAAGAAT | 4080 |
| ATCAATTTAC | CCGATATTAA | TACTCACAAA | GGAAGATTCA | CTTTAACGTT | GGATAATGGA | 4140 |
| GTGCATTGTG | TTACTACACC | AGAATACAAC | ATGGACGACC | ATAATGTTGC | CATAGGTAAA | 4200 |
| GAATTTGAGT | TGACAGTTGC | TGATTCATTA | GAGTTTATTT | TAACTTTGAA | GGCATCATAT | 4260 |
| GAAAACCTC | GTGGTACATT | AGTAGAAGTG | ACTGAAAAGA | AAGTTGTCAA | ATCAAGAAAT | 4320 |
| AGATTGAGTC | GATTATTTGG | ATCGAAAGAT | ATTATCACCA | CGACAAAGTT | TGTGCCCACT | 4380 |
| GAAGTCAAAG | ATACCTGGGC | TAATAAGTTT | GCTCCTGATG | GTTCATTTGC | TAGATGTTAC | 4440 |
| ATTGATTTAC | AACAATTTGA | AGACCAAATC | ACCGGTAAAG | CATCACAGTT | TGATCTCAAT | 4500 |
| TGTTTTAATG | AATGGGAAAC | TATGAGTAAT | GGCAATCAAC | CAATGAAAAG | AGGCAAACCT | 4560 |
| TATAAGATTG | CTCAATTGGA | AGTTAAAATG | TTGTATGTTC | CACGATCAGA | TCCAAGAGAA | 4620 |
| ATATTACCAA | CCAGCATTAG | ATCCGCATAT | GAAAGCATCA | ATGAATTAAA | CAATGAACAG | 4680 |
| AATAATTACT | TTGAAGGTTA | TTTACATCAA | GAAGGAGGTG | ATTGTCCAAT | TTTTAAGAAA | 4740 |
| CGTTTTTTCA | AATTAATGGG | CACTTCTTTA | TTGGCTCATA | GTGAAATATC | TCATAAAACT | 4800 |

```
AGAGCCAAAA  TTAATTTATC  AAAAGTTGTT  GATTTGATTT  ATGTTGATAA  AGAAAACATT    4860

GATCGTTCCA  ATCATCGAAA  TTTCAGTGAT  GTGTTATTGT  TGGATCATGC  ATTCAAAATC    4920

AAATTTGCTA  ATGGTGAGTT  GATTGATTTT  TGTGCTCCTA  ATAAACATGA  AATGAAAATA    4980

TGGATTCAAA  ATTTACAAGA  AATTATCTAT  AGAAATCGGT  TCAGACGTCA  ACCATGGGTA    5040

AATTTGATGC  TTCAACAACA  ACAACAACAA  CAACAACAAC  AAAGCTCCCA  ACAGTAATTG    5100

AAAGGTCTAC  TTTTGATTTT  TTTAATTTTA  ATTGGCAAAT  ATATGCCCAT  TTTGTATTAT    5160

CTTTTAGTCT  AATAGCGTTT  TCTTTTTTTC  CAGT                                  5194
```

( 2 ) INFORMATION FOR SEQ ID NO:2:

( i ) SEQUENCE CHARACTERISTICS:
        ( A ) LENGTH: 1664 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Met  Asn  Ser  Thr  Pro  Ser  Lys  Leu  Leu  Pro  Ile  Asp  Lys  His  Ser  His
 1                  5                        10                            15

Leu  Gln  Leu  Gln  Pro  Gln  Ser  Ser  Ala  Ser  Ile  Phe  Asn  Ser  Pro
               20                       25                       30

Thr  Lys  Pro  Leu  Asn  Phe  Pro  Arg  Thr  Asn  Ser  Lys  Pro  Ser  Leu  Asp
          35                       40                       45

Pro  Asn  Ser  Ser  Ser  Asp  Thr  Tyr  Thr  Ser  Glu  Gln  Asp  Gln  Glu  Lys
     50                       55                       60

Gly  Lys  Glu  Glu  Lys  Lys  Asp  Thr  Ala  Phe  Gln  Thr  Ser  Phe  Asp  Arg
 65                      70                       75                       80

Asn  Phe  Asp  Leu  Asp  Asn  Ser  Ile  Asp  Ile  Gln  Gln  Thr  Ile  Gln  His
                85                       90                       95

Gln  Gln  Gln  Gln  Pro  Gln  Gln  Gln  Gln  Leu  Ser  Gln  Thr  Asp  Asn
               100                      105                      110

Asn  Leu  Ile  Asp  Glu  Phe  Ser  Phe  Gln  Thr  Pro  Met  Thr  Ser  Thr  Leu
               115                      120                      125

Asp  Leu  Thr  Lys  Gln  Asn  Pro  Thr  Val  Asp  Lys  Val  Asn  Glu  Asn  His
          130                      135                      140

Ala  Pro  Thr  Tyr  Ile  Asn  Thr  Ser  Pro  Asn  Lys  Ser  Ile  Met  Lys  Lys
145                      150                      155                      160

Ala  Thr  Pro  Lys  Ala  Ser  Pro  Lys  Lys  Val  Ala  Phe  Thr  Val  Thr  Asn
                    165                      170                      175

Pro  Glu  Ile  His  His  Tyr  Pro  Asp  Asn  Arg  Val  Glu  Glu  Asp  Gln
               180                      185                      190

Ser  Gln  Gln  Lys  Glu  Asp  Ser  Val  Glu  Pro  Pro  Leu  Ile  Gln  His  Gln
          195                      200                      205

Trp  Lys  Asp  Pro  Ser  Gln  Phe  Asn  Tyr  Ser  Asp  Glu  Asp  Thr  Asn  Ala
          210                      215                      220

Ser  Val  Pro  Pro  Thr  Pro  Pro  Leu  His  Thr  Thr  Lys  Pro  Thr  Phe  Ala
225                      230                      235                      240

Gln  Leu  Leu  Asn  Lys  Asn  Asn  Glu  Val  Asn  Ser  Glu  Pro  Glu  Ala  Leu
                    245                      250                      255

Thr  Asp  Met  Lys  Leu  Lys  Arg  Glu  Asn  Phe  Ser  Asn  Leu  Ser  Leu  Asp
               260                      265                      270

Glu  Lys  Val  Asn  Leu  Tyr  Leu  Ser  Pro  Thr  Asn  Asn  Asn  Ser  Lys
               275                      280                      285
```

```
Asn  Val  Ser  Asp  Met  Asp  Ser  His  Leu  Gln  Asn  Leu  Gln  Asp  Ala  Ser
290            295                     300

Lys  Asn  Lys  Thr  Asn  Glu  Asn  Ile  His  Asn  Leu  Ser  Phe  Ala  Leu  Lys
305                 310                     315                          320

Ala  Pro  Lys  Asn  Asp  Ile  Glu  Asn  Pro  Leu  Asn  Ser  Leu  Thr  Asn  Ala
                    325                     330                     335

Asp  Ile  Ser  Leu  Arg  Ser  Ser  Gly  Ser  Gln  Ser  Ser  Leu  Gln  Ser
                    340                     345                     350

Leu  Arg  Asn  Asp  Asn  Arg  Val  Leu  Glu  Ser  Val  Pro  Gly  Ser  Pro  Lys
               355                     360                     365

Lys  Val  Asn  Pro  Gly  Leu  Ser  Leu  Asn  Asp  Gly  Ile  Lys  Gly  Phe  Ser
370                           375                     380

Asp  Glu  Val  Val  Glu  Ser  Leu  Leu  Pro  Arg  Asp  Leu  Ser  Arg  Asp  Lys
385                      390                     395                          400

Leu  Glu  Thr  Thr  Lys  Glu  His  Asp  Ala  Pro  Glu  His  Asn  Asn  Glu  Asn
                    405                     410                          415

Phe  Ile  Asp  Ala  Lys  Ser  Thr  Asn  Thr  Asn  Lys  Gly  Gln  Leu  Leu  Val
               420                     425                     430

Ser  Ser  Asp  Asp  His  Leu  Asp  Ser  Phe  Asp  Arg  Ser  Tyr  Asn  His  Thr
          435                     440                     445

Glu  Gln  Ser  Ile  Leu  Asn  Leu  Asn  Ser  Ala  Gln  Ser  Gln  Ile
     450                     455                     460

Ser  Leu  Asn  Ala  Leu  Glu  Lys  Gln  Arg  Gln  Thr  Gln  Glu  Gln  Glu  Gln
465                      470                     475                          480

Thr  Gln  Ala  Ala  Glu  Pro  Glu  Glu  Thr  Ser  Phe  Ser  Asp  Asn  Ile
                    485                     490                     495

Lys  Val  Lys  Gln  Glu  Pro  Lys  Ser  Asn  Leu  Glu  Phe  Val  Lys  Val  Thr
               500                     505                     510

Ile  Lys  Lys  Glu  Pro  Val  Ser  Ala  Thr  Glu  Ile  Lys  Ala  Pro  Lys  Arg
          515                     520                     525

Glu  Phe  Ser  Ser  Arg  Ile  Leu  Arg  Ile  Lys  Asn  Glu  Asp  Glu  Ile  Ala
     530                     535                     540

Glu  Pro  Ala  Asp  Ile  His  Pro  Lys  Lys  Glu  Asn  Glu  Ala  Asn  Ser  His
545                      550                     555                          560

Val  Glu  Asp  Thr  Asp  Ala  Leu  Leu  Lys  Lys  Ala  Leu  Asn  Asp  Asp  Glu
               565                     570                     575

Glu  Ser  Asp  Thr  Thr  Gln  Asn  Ser  Thr  Lys  Met  Ser  Ile  Arg  Phe  His
               580                     585                     590

Ile  Asp  Ser  Asp  Trp  Lys  Leu  Glu  Asp  Ser  Asn  Asp  Gly  Asp  Arg  Glu
          595                     600                     605

Asp  Asn  Asp  Asp  Ile  Ser  Arg  Phe  Glu  Lys  Ser  Asp  Ile  Leu  Asn  Asp
     610                     615                     620

Val  Ser  Gln  Thr  Ser  Asp  Ile  Ile  Gly  Asp  Lys  Tyr  Gly  Asn  Ser  Ser
625                      630                     635                          640

Ser  Glu  Ile  Thr  Thr  Lys  Thr  Leu  Ala  Pro  Pro  Arg  Ser  Asp  Asn  Asn
                    645                     650                          655

Asp  Lys  Glu  Asn  Ser  Lys  Ser  Leu  Glu  Asp  Pro  Ala  Asn  Asn  Glu  Ser
               660                     665                     670

Leu  Gln  Gln  Gln  Leu  Glu  Val  Pro  His  Thr  Lys  Glu  Asp  Asp  Ser  Ile
          675                     680                     685

Leu  Ala  Asn  Ser  Ser  Asn  Ile  Ala  Pro  Pro  Glu  Glu  Leu  Thr  Leu  Pro
690                      695                     700

Val  Val  Glu  Ala  Asn  Asp  Tyr  Ser  Ser  Phe  Asn  Asp  Val  Thr  Lys  Thr
```

-continued

```
                705                      710                     715                      720
     Phe  Asp  Ala  Tyr  Ser  Ser  Phe  Glu  Glu  Ser  Leu  Ser  Arg  Glu  His  Glu
                         725                      730                     735

Thr  Asp  Ser  Lys  Pro  Ile  Asn  Phe  Ile  Ser  Ile  Trp  His  Lys  Gln  Glu
                         740                      745                     750

Lys  Gln  Lys  Lys  His  Gln  Ile  His  Lys  Val  Pro  Thr  Lys  Gln  Ile  Ile
                         755                      760                     765

Ala  Ser  Tyr  Gln  Gln  Tyr  Lys  Asn  Glu  Gln  Glu  Ser  Arg  Val  Thr  Ser
                         770                      775                     780

Asp  Lys  Val  Lys  Ile  Pro  Asn  Ala  Ile  Gln  Phe  Lys  Lys  Phe  Lys  Glu
     785                      790                      795                          800

Val  Asn  Val  Met  Ser  Arg  Arg  Val  Val  Ser  Pro  Asp  Met  Asp  Asp  Leu
                         805                      810                          815

Asn  Val  Ser  Gln  Phe  Leu  Pro  Glu  Leu  Ser  Glu  Asp  Ser  Gly  Phe  Lys
                         820                      825                     830

Asp  Leu  Asn  Phe  Ala  Asn  Tyr  Ser  Asn  Asn  Thr  Asn  Arg  Pro  Arg  Ser
                         835                      840                     845

Phe  Thr  Pro  Leu  Ser  Thr  Lys  Asn  Val  Leu  Ser  Asn  Ile  Asp  Asn  Asp
                         850                      855                     860

Pro  Asn  Val  Val  Glu  Pro  Pro  Glu  Pro  Lys  Ser  Tyr  Ala  Glu  Ile  Arg
     865                      870                      875                          880

Asn  Ala  Arg  Arg  Leu  Ser  Ala  Asn  Lys  Ala  Ala  Pro  Asn  Gln  Ala  Pro
                         885                      890                     895

Pro  Leu  Pro  Pro  Gln  Arg  Gln  Pro  Ser  Ser  Thr  Arg  Ser  Asn  Ser  Asn
                         900                      905                     910

Lys  Arg  Val  Ser  Arg  Phe  Arg  Val  Pro  Thr  Phe  Glu  Ile  Arg  Arg  Thr
                         915                      920                     925

Ser  Ser  Ala  Leu  Ala  Pro  Cys  Asp  Met  Tyr  Asn  Asp  Ile  Phe  Asp  Asp
                         930                      935                     940

Phe  Gly  Ala  Gly  Ser  Lys  Pro  Thr  Ile  Lys  Ala  Glu  Gly  Met  Lys  Thr
     945                      950                      955                          960

Leu  Pro  Ser  Met  Asp  Lys  Asp  Val  Lys  Arg  Ile  Leu  Asn  Ala  Lys
                         965                      970                          975

Lys  Gly  Val  Thr  Gln  Asp  Glu  Tyr  Ile  Asn  Ala  Lys  Leu  Val  Asp  Gln
                         980                      985                     990

Lys  Pro  Lys  Lys  Asn  Ser  Ile  Val  Thr  Asp  Pro  Glu  Asp  Arg  Tyr  Glu
                         995                     1000                    1005

Glu  Leu  Gln  Gln  Thr  Ala  Ser  Ile  His  Asn  Ala  Thr  Ile  Asp  Ser  Ser
                        1010                     1015                    1020

Ile  Tyr  Gly  Arg  Pro  Asp  Ser  Ile  Ser  Thr  Asp  Met  Leu  Pro  Tyr  Leu
     1025                     1030                     1035                         1040

Ser  Asp  Glu  Leu  Lys  Lys  Pro  Pro  Thr  Ala  Leu  Leu  Ser  Ala  Asp  Arg
                        1045                     1050                    1055

Leu  Phe  Met  Glu  Gln  Glu  Val  His  Pro  Leu  Arg  Ser  Asn  Ser  Val  Leu
                        1060                     1065                    1070

Val  His  Pro  Gly  Ala  Gly  Ala  Ala  Thr  Asn  Ser  Ser  Met  Leu  Pro  Glu
                        1075                     1080                    1085

Pro  Asp  Phe  Glu  Leu  Ile  Asn  Ser  Pro  Ala  Arg  Asn  Val  Ser  Asn  Asn
                        1090                     1095                    1100

Ser  Asp  Asn  Val  Ala  Ile  Ser  Gly  Asn  Ala  Ser  Thr  Ile  Ser  Phe  Asn
     1105                     1110                     1115                         1120

Gln  Leu  Asp  Met  Asn  Phe  Asp  Asp  Gln  Ala  Thr  Ile  Gly  Gln  Lys  Ile
                        1125                     1130                    1135
```

```
Gln Glu Gln Pro Ala Ser Lys Ser Ala Asn Thr Val Arg Gly Asp Asp
             1140                1145                1150

Asp Gly Leu Ala Ser Ala Pro Glu Thr Pro Arg Thr Pro Thr Lys Lys
             1155                1160                1165

Glu Ser Ile Ser Ser Lys Pro Ala Lys Leu Ser Ser Ala Ser Pro Arg
             1170                1175                1180

Lys Ser Pro Ile Lys Ile Gly Ser Pro Val Arg Val Ile Lys Lys Asn
1185             1190                1195                1200

Gly Ser Ile Ala Gly Ile Glu Pro Ile Pro Lys Ala Thr His Lys Pro
             1205                1210                1215

Lys Lys Ser Phe Gln Gly Asn Glu Ile Ser Asn His Lys Val Arg Asp
             1220                1225                1230

Gly Gly Ile Ser Pro Ser Ser Gly Ser Glu His Gln Gln His Asn Pro
             1235                1240                1245

Ser Met Val Ser Val Pro Ser Gln Tyr Thr Asp Ala Thr Ser Thr Val
             1250                1255                1260

Pro Asp Glu Asn Lys Asp Val Gln His Lys Pro Arg Glu Lys Gln Lys
1265             1270                1275                1280

Gln Lys His His His Arg His His His His His Lys Gln Lys Thr
             1285                1290                1295

Asp Ile Pro Gly Val Val Asp Asp Glu Ile Pro Asp Val Gly Leu Gln
             1300                1305                1310

Glu Arg Gly Lys Leu Phe Phe Arg Val Leu Gly Ile Lys Asn Ile Asn
             1315                1320                1325

Leu Pro Asp Ile Asn Thr His Lys Gly Arg Phe Thr Leu Thr Leu Asp
             1330                1335                1340

Asn Gly Val His Cys Val Thr Thr Pro Glu Tyr Asn Met Asp Asp His
1345             1350                1355                1360

Asn Val Ala Ile Gly Lys Glu Phe Glu Leu Thr Val Ala Asp Ser Leu
             1365                1370                1375

Glu Phe Ile Leu Thr Leu Lys Ala Ser Tyr Glu Lys Pro Arg Gly Thr
             1380                1385                1390

Leu Val Glu Val Thr Glu Lys Lys Val Val Lys Ser Arg Asn Arg Leu
             1395                1400                1405

Ser Arg Leu Phe Gly Ser Lys Asp Ile Ile Thr Thr Thr Lys Phe Val
             1410                1415                1420

Pro Thr Glu Val Lys Asp Thr Trp Ala Asn Lys Phe Ala Pro Asp Gly
1425             1430                1435                1440

Ser Phe Ala Arg Cys Tyr Ile Asp Leu Gln Gln Phe Glu Asp Gln Ile
             1445                1450                1455

Thr Gly Lys Ala Ser Gln Phe Asp Leu Asn Cys Phe Asn Glu Trp Glu
             1460                1465                1470

Thr Met Ser Asn Gly Asn Gln Pro Met Lys Arg Gly Lys Pro Tyr Lys
             1475                1480                1485

Ile Ala Gln Leu Glu Val Lys Met Leu Tyr Val Pro Arg Ser Asp Pro
             1490                1495                1500

Arg Glu Ile Leu Pro Thr Ser Ile Arg Ser Ala Tyr Glu Ser Ile Asn
1505             1510                1515                1520

Glu Leu Asn Asn Glu Gln Asn Asn Tyr Phe Glu Gly Tyr Leu His Gln
             1525                1530                1535

Glu Gly Gly Asp Cys Pro Ile Phe Lys Lys Arg Phe Phe Lys Leu Met
             1540                1545                1550

Gly Thr Ser Leu Leu Ala His Ser Glu Ile Ser His Lys Thr Arg Ala
             1555                1560                1565
```

```
Lys  Ile  Asn  Leu  Ser  Lys  Val  Val  Asp  Leu  Ile  Tyr  Val  Asp  Lys  Glu
     1570                1575                1580

Asn  Ile  Asp  Arg  Ser  Asn  His  Arg  Asn  Phe  Ser  Asp  Val  Leu  Leu  Leu
1585                1590                1595                               1600

Asp  His  Ala  Phe  Lys  Ile  Lys  Phe  Ala  Asn  Gly  Glu  Leu  Ile  Asp  Phe
               1605                1610                               1615

Cys  Ala  Pro  Asn  Lys  His  Glu  Met  Lys  Ile  Trp  Ile  Gln  Asn  Leu  Gln
          1620                1625                               1630

Glu  Ile  Ile  Tyr  Arg  Asn  Arg  Phe  Arg  Arg  Gln  Pro  Trp  Val  Asn  Leu
     1635                1640                1645

Met  Leu  Gln  Gln  Gln  Gln  Gln  Gln  Gln  Gln  Gln  Gln  Ser  Ser  Gln  Gln
     1650                1655                1660
```

(2) INFORMATION FOR SEQ ID NO:3:

(i) SEQUENCE CHARACTERISTICS:
        (A) LENGTH: 236 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: amino acid positions 218-453 from SEQ ID NO:2

(xi) SEQUENCE DESCRIPTION: SEQ ID NO:3:

```
Ser  Asp  Glu  Asp  Thr  Asn  Ala  Ser  Val  Pro  Thr  Pro  Pro  Leu  His
1                    5                    10                       15

Thr  Thr  Lys  Pro  Thr  Phe  Ala  Gln  Leu  Leu  Asn  Lys  Asn  Asn  Glu  Val
               20                    25                    30

Asn  Ser  Glu  Pro  Glu  Ala  Leu  Thr  Asp  Met  Lys  Leu  Lys  Arg  Glu  Asn
          35                    40                    45

Phe  Ser  Asn  Leu  Ser  Leu  Asp  Glu  Lys  Val  Asn  Leu  Tyr  Leu  Ser  Pro
     50                    55                    60

Thr  Asn  Asn  Asn  Asn  Ser  Lys  Asn  Val  Ser  Asp  Met  Asp  Ser  His  Leu
65                    70                    75                            80

Gln  Asn  Leu  Gln  Asp  Ala  Ser  Lys  Asn  Lys  Thr  Asn  Glu  Asn  Ile  His
               85                    90                    95

Asn  Leu  Ser  Phe  Ala  Leu  Lys  Ala  Pro  Lys  Asn  Asp  Ile  Glu  Asn  Pro
               100                   105                   110

Leu  Asn  Ser  Leu  Thr  Asn  Ala  Asp  Ile  Ser  Leu  Arg  Ser  Ser  Gly  Ser
               115                   120                   125

Ser  Gln  Ser  Ser  Leu  Gln  Ser  Leu  Arg  Asn  Asp  Asn  Arg  Val  Leu  Glu
     130                   135                   140

Ser  Val  Pro  Gly  Ser  Pro  Lys  Lys  Val  Asn  Pro  Gly  Leu  Ser  Leu  Asn
145                   150                   155                            160

Asp  Gly  Ile  Lys  Gly  Phe  Ser  Asp  Glu  Val  Val  Glu  Ser  Leu  Leu  Pro
                    165                   170                        175

Arg  Asp  Leu  Ser  Arg  Asp  Lys  Leu  Glu  Thr  Thr  Lys  Glu  His  Asp  Ala
               180                   185                   190

Pro  Glu  His  Asn  Asn  Glu  Asn  Phe  Ile  Asp  Ala  Lys  Ser  Thr  Asn  Thr
          195                   200                   205

Asn  Lys  Gly  Gln  Leu  Leu  Val  Ser  Ser  Asp  Asp  His  Leu  Asp  Ser  Phe
     210                   215                   220

Asp  Arg  Ser  Tyr  Asn  His  Thr  Glu  Gln  Ser  Ile  Leu
225                   230                   235
```

( 2 ) INFORMATION FOR SEQ ID NO:4:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Tyr  Leu  Ser  Pro  Thr  Asn  Asn  Asn  Asn  Ser  Lys  Asn  Val  Ser  Asp  Met
1                  5                        10                       15
Asp  Leu  His  Leu  Gln  Asn  Leu
               20
```

( 2 ) INFORMATION FOR SEQ ID NO:5:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

```
Asp  Trp  Lys  Leu  Glu  Asp  Ser  Asn  Asp  Gly  Asp  Arg  Glu  Asp  Asn  Asp
1                  5                        10                       15
Asp  Ile  Ser  Arg  Phe  Glu  Lys
               20
```

( 2 ) INFORMATION FOR SEQ ID NO:6:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ser  Lys  Ser  Ala  Asn  Thr  Val  Arg  Gly  Asp  Asp  Asp  Gly  Leu  Ala  Ser
1                  5                        10                       15
Ala
```

( 2 ) INFORMATION FOR SEQ ID NO:7:

( i ) SEQUENCE CHARACTERISTICS:
        ( A ) LENGTH: 17 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Asp  His  Leu  Asp  Ser  Phe  Asp  Arg  Ser  Tyr  Asn  His  Thr  Glu  Gln  Ser
1                  5                        10                       15
Ile
```

( 2 ) INFORMATION FOR SEQ ID NO:8:

( i ) SEQUENCE CHARACTERISTICS:
        ( A ) LENGTH: 17 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:8:

Trp Ile Gln Asn Leu Gln Glu Ile Ile Tyr Arg Asn Arg Phe Arg Arg
1               5                   10                  15

Gln (2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:9:

GAATTCAATG CTACCCTCAA                                                   20

(2) INFORMATION FOR SEQ ID NO:10:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

CCCGGGGGAC CCCCTTCACT                                                   20

(2) INFORMATION FOR SEQ ID NO:11:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

AARGTYGGWT TYTTYAAR                                                     18

(2) INFORMATION FOR SEQ ID NO:12:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GAAATHGAYG AYTTRATG                                                     18

CANDIDA ALBICANS INTEGRIN-LIKE PROTEIN

STATEMENT OF GOVERNMENT RIGHTS

This invention was made with government support under Grant No. R-01 AI25827, awarded by the National Institutes of Health. The government has certain rights in the present invention.

BACKGROUND OF THE INVENTION

Candida albicans is the leading fungal pathogen in normal hosts and in patients with damaged immune systems. In normal hosts, disease caused by C. albicans ranges from mild, easily treated, superficial disease (e.g., thrush in newborn infants; paronychia in workers whose hands are immersed in water) to more severe, chronic or recurrent infections (e.g., candidal vaginitis). It is estimated that 5% of women of child-bearing age will suffer from recurrent candidal vaginitis (Hurley, "Trends in candidal vaginitis." Proc. R. Soc. Med. 70 (Suppl. 4), 1–8 (1970), and that virtually every woman will experience at least one episode during her reproductive years. Vaginitis is particularly frequent in otherwise normal females with diabetes or a history of prolonged antibiotic or oral contraceptive use. While short-term topical therapy is effective in treating individual episodes of vaginitis, such agents do not prevent recurrences. Thus, even in the normal host, infection with C. albicans can occur at epithelial surfaces, and recurrences are not prevented by presently available therapies.

In immunocompromised hosts such as cancer patients, transplant patients, post-operative surgical patients, premature newborns, or HIV-infected people, C. albicans ranks as the leading fungal pathogen. In this population, disease ranges from aggressive local infections such as periodontitis, oral ulceration, or esophagitis in HIV-infected patients, to complex and potentially lethal infections of the bloodstream with subsequent dissemination to brain, eye, heart, liver, spleen, kidneys, or bone. Such grave prognoses require more toxic therapy, with attendant consequences from both the underlying infection and the treatment. Here again, the infection typically begins at an epithelial site, evades local defenses, and invades the bloodstream in the face of immunosuppression. Strategies to interrupt candidal adhesion therefore have broad applicability to the prevention of mild but recurrent disease in the normal host and to the reduction of substantial morbidity and mortality in the immunocompromised.

It is well recognized that C. albicans adheres to epithelial and endothelial cells in the human host, oftentimes by recognizing proteins of the extracellular matrix called ligands. These ligands include proteins such as fibronectin, vitronectin, fibrinogen, the C3 degradation fragment iC3b, or the shorter C3 degradation fragment C3d. Because recognition of all of these proteins except C3d is dependent upon the amino acid sequence ARGININE-GLYCINE-ASPARTIC ACID or R-G-D, these candidal adhesions are thought to operate like the vertebrate integrins and are called "integrin-like proteins" or "integrin analogs."

Vertebrate integrins are composed of two subunits: an α-subunit and a β-subunit. There are approximately 14 α and 8 β subunits described to date in vertebrate cells. Using monoclonal or polyclonal antibodies to vertebrate integrins, several investigators have obtained evidence for integrin-like proteins in C. albicans: an αM analog, an α 5/β1 complex, or a β1 analog. Neither the α 5/β1 complex nor the β1 analog has been isolated from C. albicans or from any other candidal species, and the responsible genes encoding these "integrin-like proteins" have not been identified.

SUMMARY OF THE INVENTION

The present invention provides an isolated and purified DNA molecule encoding a Candida albicans protein with integrin-like motifs that hybridizes to DNA complementary to DNA having SEQ ID NO:1 under the stringency conditions of hybridization in buffer containing 5× SSC, 5× Denhardt's, 0.5% SDS, 1 mg salmon sperm/25 mls of hybridization solution incubated at 65° C. overnight, followed by high stringency washing with 0.2× SSC/0.1% SDS at 65° C. Preferably, the present invention provides an isolated and purified DNA molecule encoding the Candida albicans protein with integrin-like motifs which has the amino acid sequence having SEQ ID NO:2. Preferably, the DNA is genomic DNA which has the nucleotide sequence shown in Table 1 (SEQ ID NO:1).

The present invention also provides a vector and a cell line transformed by an extrachromosomal plasmid containing non-native DNA encoding Candida albicans protein with integrin-like motifs (i.e., C. albicans integrin-like protein), as described herein. The cell line preferably comprises S. cerevisiae. This cell line can be used in a method of delivering a gene product to a subject.

The present invention also provides a Candida albicans protein with integrin-like motifs comprising an I domain, two EF-hand divalent cation binding sites, a sequence sufficient to encode a transmembrane domain, an internal RGD tripeptide, and a carboxy-terminal sequence with a single tyrosine residue. As used herein, an "internal" RGD tripeptide means that the RGD sequence is in the Candida protein, not in the vertebrate proteins recognized by integrins. Preferably, the isolated and purified C. albicans integrin-like protein has an amino acid sequence which is SEQ ID NO:2. Also provided are isolated and purified peptides, such as those having an amino acid sequence selected from the group consisting of: YLS PTN NNN SKN VSD MDL HLQ NL (SEQ ID NO:4); DWK LED SND GDR EDN DDI SRF EK (SEQ ID NO:5); SKS ANT VRG DDD GLA SA (SEQ ID NO:6); DHL DSF DRS YNH TEQ SI (SEQ ID NO:7); and WIQ NLQ EII YRN RFR RQ (SEQ ID NO:8). The invention also provides a vaccine comprising the protein and peptides, either singly or together, described herein as well as an isolated and purified antibodies to the C. albicans integrin-like protein and peptides described herein.

The invention also provides a method of inhibiting adhesion of Candida albicans to cells (preferably epithelial cells, and more preferably human epithelial cells). The method includes contacting the Candida albicans with antibodies to the Candida albicans protein with integrin-like motifs (αInt1p) or to fragments thereof as described herein.

DETAILED DESCRIPTION

Figure 1:
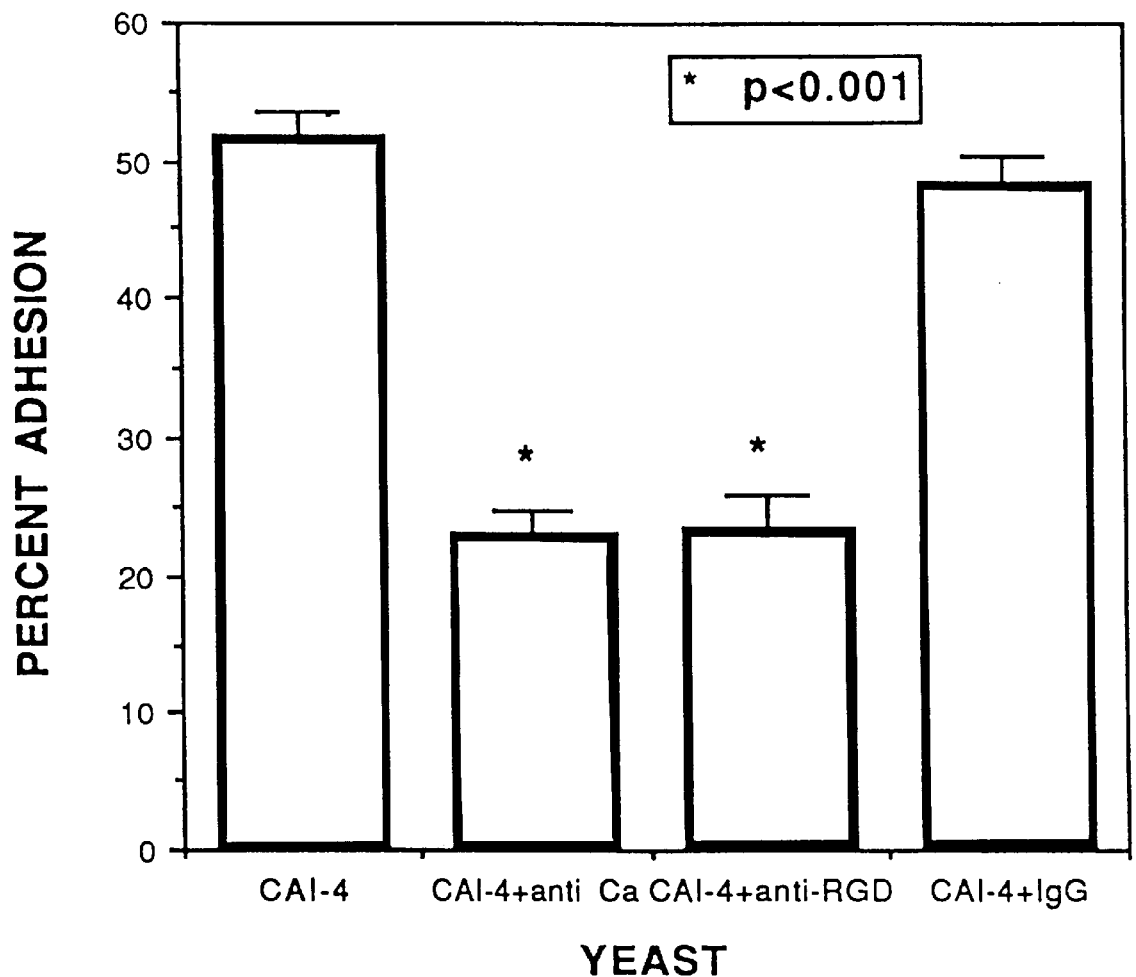
FIG. 1 is a graph of the blockade of candidal adhesion to HeLa cells by antibodies to αInt1p.

Specifically, the present invention is directed to the cloning and expression of a gene (αINT1) for an integrin-like protein (αInt1p) of Candida albicans. To that end, the invention provides an isolated and purified DNA molecule encoding a Candida albicans protein with an integrin-like motifs or biologically active derivative thereof. More preferably, the DNA is a genomic DNA molecule that encodes the protein represented by the amino acid sequence shown in Table 2 (SEQ ID NO:2). Most preferably, the genomic DNA molecule is represented by the complete nucleotide sequence shown in Table 1 (SEQ ID NO:1). Isolated and purified peptides encoded by this DNA, and derivatives thereof, which are biologically active are also within the scope of the invention.

As used herein, the terms "isolated and purified" refer to in vitro isolation of a DNA molecule or protein from its natural cellular environment, and from association with other coding regions of the C. albicans genome, so that it can be sequenced, replicated, and/or expressed. Preferably, the isolated and purified DNA molecules of the invention comprise a single coding region. Thus, the present DNA molecules are those consisting essentially of a DNA segment encoding an integrin-like protein or biologically active derivative thereof. Although the DNA molecule includes a single coding region, it can contain additional nucleotides that do not detrimentally affect the function of the DNA molecule, i.e., the expression of the integrin-like protein or biologically active derivative thereof. For example, the 5' and 3' untranslated regions may contain variable numbers of nucleotides. Preferably, additional nucleotides are outside the single coding region.

The present invention also provides an isolated and purified DNA molecule that encodes integrin-like protein (αInt1p) and that hybridizes to a DNA molecule complementary to the DNA molecule shown in Table 1 (SEQ ID NO:1) under high stringency hybridization conditions. As used herein, "high stringency hybridization conditions" refers to hybridization in buffer containing 5× SSC, 5× Denhardt's, 0.5% SDS, 1 mg salmon sperm/25 mls of hybridization solution incubated at 65° C. overnight, followed by high stringency washing with 0.2× SSC/0.1% SDS at 65° C.

It is envisioned that oligonucleotdies are also possible. Oligonucleotide probes and primers are segments of labeled, single-stranded DNA which will hybridize, or noncovalently bind, with complementary single-stranded DNA to be identified.

If desired, the probe and primer can be labeled with any suitable label known to those skilled in the art, including radioactive and nonradioactive labels. Typical radioactive labels include $^{32}P$, $^{125}I$, $^{35}S$, and the like. Nonradioactive labels include, for example, ligands such as biotin or digoxigenin as well as enzymes such as phosphatase or peroxidases, or the various chemiluminescers such as luciferin, or fluorescent compounds like fluorescein and its derivatives. The probe or primer may also be labeled at both ends with different types of labels for ease of separation, as, for example, by using an isotopic label at one end and a biotin label at the other end.

As used herein, the terms "protein with integrin-like motifs" and "integrin-like protein" refer to a candidal adhesin of C. albicans, that is expressed at the surface of C. albicans and allows candida to bind to epithelial cells, for example. This initial adhesion to epithelium leads to subsequent events in the pathogenesis of invasive candidal infection (e.g., penetration of epithelial barriers and hematogenous dissemination). The unmodified protein (i.e., prior to any post-translational modification) is preferably of about 180–190 kDa, and more preferably of about 188 kDa. It includes several motifs common to αM and αX leukocyte integrins. These motifs include: (1) an Inserted domain ("I" domain) containing a conformationally dependent cation binding site (or MIDAS motif, as disclosed in Michishita et al., Cell, 72, 857–867 (1993)); (2) two linear divalent cation binding sites conforming to the EF-hand motif; (3) a sequence sufficient to encode a transmembrane domain; (4) a carboxy-terminal sequence with a single tyrosine residue; and (5) an internal RGD tripeptide (arginine-glycine-aspartic acid). The RGD site is at amino acids 1149–1151 in SEQ ID NO:2.

A "biologically active derivative thereof" is an integrin-like protein that is modified by amino acid deletion, addition, substitution, or truncation, or that has been chemically derivatized, but that nonetheless functions in the same manner as the protein of SEQ ID NO:2. For example, it is known in the art that substitutions of aliphatic amino acids such as alanine, valine and isoleucine with other aliphatic amino acids can often be made without altering the structure or function of a protein. Similarly, substitution of aspartic acid for glutamic acid, in regions other than the active site of an enzyme, are likely to have no appreciable affect on protein structure or function. The term "biologically active derivative" is intended to include C. albicans proteins with integrin-like motifs as thus modified. The term also includes fragments, variants, analogs or chemical derivatives thereof. The term "fragment" is meant to refer to any polypeptide subset. Fragments can be prepared by subjecting C. albicans proteins with integrin-like motifs to the action of any one of a number of commonly available proteases, such as trypsin, chymotrypsin or pepsin, or to chemical cleavage agents, such as cyanogen bromide. The term "variant" is meant to refer to a molecule substantially similar in structure and function to either the entire C. albicans integrin-like protein or to a fragment thereof. A protein or peptide is said to be "substantially similar" if both molecules have substantially similar amino acid sequences, preferably greater than about 80% sequence identity, or if the three-dimensional backbone structures of the molecules are superimposable, regardless of the level of identity between the amino acid sequences. Thus, provided that two molecules possess similar activity, they are considered variants as that term is used herein even if the structure of one of the molecules is not found in the other, or if the sequences of amino acid residues are not identical. The term "analog" is meant to refer to a protein that differs structurally from the wild type C. albicans integrin-like protein, but possesses similar activity.

Several fragments of the protein have been prepared and can be used in vaccines or as antigens to prepare anti-peptide antibodies, which can be monoclonal or polyclonal (preferably polyclonal). A 236 amino acid sequence near the amino terminus of the gene product (αInt1p) is shown in Table 3 (SEQ ID NO:3). A 23-mer peptide encompassing the first cation-binding site is YLS PTN NNN SKN VSD MDL HLQ NL (SEQ ID NO:4). A 23-mer peptide encompassing the second divalent cation-binding site is DWK LED SND GDR EDN DDI SRF EK (SEQ ID NO:5). A 17-mer peptide spanning the RGD site and flanking residues is SKS ANT VRG DDD GLA SA (SEQ ID NO:6). A 17-mer peptide from the MIDAS motif of αInt1p is DHL DSF DRS YNH TEQ SI (SEQ ID NO:7). A 17-mer peptide from the C-terminus of αInt1p is WIQ NLQ EII YRN RFR RQ (SEQ ID NO:8).

The antibodies produced to these peptides bind to C. albicans blastospores, germ tubes, and hyphae, and thereby block epithelial adhesion of C. albicans (i.e., candida). Preferably, the antibodies are able to block C. albicans adhesion by at least about 30%, and preferably by at least about 50%. It is believed that this blocking activity of the initial adhesion to epithelium will reduce and even prevent subsequent events in the pathogenesis of invasive candidal infection.

The present invention also provides a vector comprising an isolated and purified DNA molecule encoding C. albicans protein with integrin-like motifs or a biologically active derivative thereof, preferably C. albicans protein with integrin-like motifs having the amino acid sequence of SEQ ID NO:2. Preferably, the vector includes a sequence encoding the C. albicans protein with integrin-like motifs as well as a second DNA segment operably linked to the coding sequence and capable of directing expression of the coding region, such as a promoter region operably linked to the 5' end of the coding DNA sequence. The vector can also include a DNA segment that is a selectable marker gene or a reporter gene as well as upstream untranslated sequence from the C. albicans gene.

The present invention also provides a cell line, preferably a Saccharomyces cerevisiae yeast strain transformed with an extrachromosomal plasmid containing non-native DNA encoding the C. albicans protein with integrin-like motifs. S. cerevisiae, also known as brewer's yeast or baker's yeast, typically exhibits a spheriod, yeast-like form and, under certain conditions, can also exhibit a filamentous, mold-like form. The filamentous cells, which are often referred to as pseudohyphal cells, have an elongated morphology. S. cerevisiae (preferably haploid S. cerevisiae), which is seldom a pathogen, transformed with the open reading frame of αINT1, displays germ tube-like projections referred to herein as "noses." Thus, synthesis of the Candida gene product αInt1p in S. cerevisiae induces germ tubes. Furthermore, αInt1p is surface expressed in S. cerevisiae and can be recognized by polyclonal antibodies to αInt1p peptides and by monoclonal antibodies to vertebrate integrins. In this way, a generally harmless yeast becomes "sticky" and "nosey."

The S. cerevisiae yeast cells transformed by the gene described herein will adhere to epithelial surfaces as a result of expression of the integrin-like gene described herein; however, they will not invade the cells. Thus, "sticky" S. cerevisiae may colonize in patients at risk for Candida infection and thereby block the adhesion sites, and reduce or eliminate the opportunity for Candida to adhere, colonize, and invade. Also, the "sticky" S. cerevisiae may function as a gene or gene product delivery system. For example, it is envisioned that a phosphate-binding protein could be delivered to the gastrointestinal tract of a patient with chronic renal failure using Saccharomyces transformed by the integrin-like gene and a second plasmid for expression of the phosphate-binding protein. Alternatively, a second plasmid could be used to provide a source of vaccine antigen for gastrointestinal pathogens like cholera. In the genitourinary tract, expression of spermicides by S. cerevisiae transformed with the C. albicans integrin-like gene on an extrachromosomal plasmid could provide a cheap and infrequent method of contraception. Also, synthesis of protein-based antiretroviral agents could help to reduce transmission of HIV in the birth canal.

1. Isolation of DNA

Several different methods are available for isolating genomic DNA. Most approaches begin with the purification of protein. Purified protein is then subjected to amino acid microsequencing, either directly or after limited cleavage. The partial amino acid sequence that is obtained can be used to design degenerate oligonucleotide probes or primers for use in the generation of unique, nondegenerate nucleotide sequences by polymerase chain reaction (PCR), sequences that can in turn be used as probes for screening genomic DNA libraries. Antibodies raised against purified protein may also be used to isolate DNA clones from expression libraries.

Alternatively, the sequences of DNAs for related proteins (e.g., human integrins) may be used as starting points in a cloning strategy, so-called "cloning by homology". Another way of utilizing sequence information from different species is to take advantage of shorter areas of high sequence homology among related DNAs from different species and to perform PCR to obtain "species-specific" nondegenerate nucleotide sequences. Such a sequence can then be used for library screening or even for direct PCR-based cloning. Detection of the desired DNA can also involve the use of PCR using novel primers.

Alternatively, the region encoding αInt1p may be obtained from a genomic DNA library or by in vitro polynucleotide synthesis from the complete nucleotide acid sequence.

Libraries are screened with appropriate probes designed to identify the genomic DNA of interest. Preferably, for genomic libraries, suitable probes include oligonucleotides that consist of known or suspected portions of the αInt1p genomic DNA from the same or different species; and/or complementary or homologous genomic DNAs or fragments thereof that consist of the same or a similar DNA. For expression libraries (which express the protein), suitable probes include monoclonal or polyclonal antibodies that recognize and specifically bind to the αInt1p protein. Appropriate probes for screening genomic DNA libraries include, but are not limited to, oligonucleotides, genomic DNAs, or fragments thereof that consist of the same or a similar gene, and/or homologous genomic DNAs or fragments thereof. Screening the genomic DNA library with the selected probe may be accomplished using standard procedures.

Screening genomic DNA libraries using synthetic oligonucleotides as probes is a preferred method of practicing this invention. The oligonucleotide sequences selected as probes should be of sufficient length and sufficiently unambiguous to minimize false positives. The actual nucleotide sequence (s) of the probe(s) is usually designed based on regions of the αInt1p genomic DNA that have the least codon redundancy. The oligonucleotides may be degenerate at one or more positions, i.e., two or more different nucleotides may be incorporated into an oligonucleotide at a given position, resulting in multiple synthetic oligonucleotides. The use of degenerate oligonucleotides is of particular importance where a library is screened from a species in which preferential codon usage is not known.

The oligonucleotide can be labeled such that it can be detected upon hybridization to DNA in the library being screened. A preferred method of labeling is to use ATP and polynucleotide kinase to radiolabel the 5' end of the oligonucleotide. However, other methods may be used to label the oligonucleotide, including, but not limited to, biotinylation or enzyme labeling.

Of particular interest is the αINT1 nucleotide sequence that encodes a full-length mRNA transcript, including the complete coding region for the gene product, αInt1p. Nucleic acid containing the complete coding region can be obtained by screening selected genomic DNA libraries using an oligonucleotide encoding the deduced amino acid sequence.

An alternative means to isolate the DNA encoding αInt1p is to use PCR methodology. This method requires the use of oligonucleotide primer probes that will hybridize to the DNA encoding αInt1p. Strategies for selection of PCR primer oligonucleotides are described below.

2. Insertion of DNA into Vector

The nucleic acid containing the αINT1 coding region is preferably inserted into a replicable vector for further cloning (amplification of the DNA) or for expression of the gene product. Many vectors are available, and selection of the appropriate vector will depend on: 1) whether it is to be used for DNA amplification or for DNA expression; 2) the size of the nucleic acid to be inserted into the vector; and 3) the host cell to be transformed with the vector. Most expression vectors are "shuttle" vectors, i.e., they are capable of replication in at least one class of organism but can be transfected into another organism for expression. For example, a vector replicates in E. coli and then the same vector is transfected into yeast or mammalian cells for expression even though it is not capable of replicating independently of the host cell chromosome. Each replicable vector contains various structural components depending on its function (amplification of DNA or expression of DNA) and the host cell with which it is compatible. These components are described in detail below.

Construction of suitable vectors employs standard ligation techniques known in the art. Isolated plasmids or DNA fragments are cleaved, tailored, and religated in the form desired to generate the plasmids required. Typically, the ligation mixtures are used to transform E. coli K12 or E. coli XL1 Blue MRF strains 294 (ATCC 31,446) and successful transformants are selected by ampicillin or tetracycline resistance where appropriate. Plasmids from the transformants are prepared, analyzed by restriction endonuclease digestion, and/or sequenced by methods known in the art.

Replicable cloning and expression vector components generally include, but are not limited to, one or more of the following: an origin of replication, one or more marker genes, an enhancer element, a promoter and a transcription termination sequence.

Vector component: origin of replication. Both expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast and viruses.

Vector component: marker gene. Expression and cloning vectors may contain a marker gene, also termed a selection gene or selectable marker. This gene encodes a protein necessary for the survival or growth of transformed host cells grown in a selective culture medium. Host cells not transformed with the vector containing the selection gene will not survive in the culture medium. Typical selection genes encode proteins that: (a) confer resistance to antibiotics or other toxins, e.g., ampicillin, neomycin, methotrexate, streptomycin or tetracycline; (b) complement auxotrophic deficiencies; or (c) supply critical nutrients not available from complex media, e.g., the gene encoding D-alanine racemase for Bacillus. One example of a selection scheme utilizes a drug to arrest growth of a host cell. Those cells that are successfully transformed with a heterologous gene express a protein conferring drug resistance and thus survive the selection regimen.

A suitable marker gene for use in yeast is URA3 or the TRP1 gene present in the yeast plasmid YRp7 (Stinchcomb et al., Nature, 282, 39 (1979); Kingsman et al., Gene, 7, 141 (1979); or Tschemper et al., Gene, 10, 157 (1980)). The TRP1 gene provides a selection marker for a mutant strain of yeast lacking the ability to grow in tryptophan, for example, ATCC No. 44076 or PEP4-1 (Jones, Genetics, 85, 23 (1977)).

Vector component: promoter. Expression and cloning vectors usually contain a promoter that is recognized by the host organism and is operably linked to the gene. Promoters are untranslated sequences located upstream (5') to the start codon of a structural gene (generally within about 100 to 1000 bp) that control the transcription and translation of a particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. In contrast, constitutive promoters produce a constant level of transcription of the cloned DNA segment.

At this time, a large number of promoters recognized by a variety of potential host cells are well known in the art. Promoters are removed from their source DNA using a restriction enzyme digestion and inserted into the cloning vector using standard molecular biology techniques. Native or heterologous promoters can be used to direct amplification and/or expression of DNA. Heterologous promoters are preferred, as they generally permit greater transcription and higher yields of expressed protein as compared to the native promoter. Well-known promoters suitable for use with prokaryotic hosts include the beta-lactamase and lactose promoter systems, alkaline phosphatase, a tryptophan (trp) promoter system, and hybrid promoters such as the tac promoter. Such promoters can be ligated to the DNA to be expressed using linkers or adapters to supply any required restriction sites. Promoters for use in bacterial systems may contain a Shine-Dalgarno sequence for RNA polymerase binding.

Promoter sequences are known for eukaryotes. Virtually all eukaryotic genes have an AT-rich region located approximately 25 to 30 bp upstream from the site where transcription is initiated Another sequence found 70 to 80 bases upstream from the start of transcription of many genes is the CXCAAT region where X may be any nucleotide. At the 3' end of most eukaryotic genes is an AATAAA sequence that may be a signal for addition of the poly A tail to the 3' end of the coding sequence. All these sequences are suitably inserted into eukaryotic expression vectors. Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase and glucokinase. Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization.

Vector component: enhancer element. Transcription of DNA by higher eukaryotes can be increased by inserting an enhancer sequence into the vector. Enhancers are cis-acting elements of DNA, usually having about 10 to 300 bp, that act on a promoter to increase its transcription. Enhancers are relatively orientation-and position-independent, having been found 5' and 3' to the transcription unit, within an intron as well as within the coding sequence itself. Typically, an enhancer from a eukaryotic cell virus will be used. Examples include the SV40 enhancer on the late side of the replication origin, the cytomegalovirus early promoter enhancer, the polyoma enhancer on the late side of the replication origin, and adenovirus enhancers. The enhancer may be spliced into the vector at a position 5' or 3' to the DNA, but is preferably located at a site 5' of the promoter.

Vector component: transcription termination. Expression vectors used in eukaryotic host cells (e.g., yeast, fungi, etc.) can also contain sequences necessary for the termination of transcription and for stabilizing the mRNA. Such sequences are commonly available from the 5' and, occasionally, 3' untranslated regions of eukaryotic or viral DNAs. These regions can contain nucleotide segments transcribed as polyadenylated fragments in the untranslated portion of the mRNA.

The genetically engineered plasmid of the invention can be used to transform a host cell. As discussed above, a particularly desirable host is a eukaryotic microbe such as filamentous fungi or yeast. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe*, Kluyveromyces hosts such as, e.g., *K. lactis, K. fragilis, K. bulgaricus, K. thermotolerans*, and *K. marxianus*, yarrowia, *Pichia pastoris, Trichoderma reesia, Neurospora crassa*, and filamentous fungi such as, e.g., Neurospora, Penicillium, Tolypocladium, and Aspergillus hosts such as *A. nidulans*.

4. Transfection and Transformation

Host cells are transfected and preferably transformed with the above-described expression or cloning vectors of this invention and cultured in conventional nutrient media modified as appropriate for inducing promoters, selecting transformants, or amplifying the genes encoding the desired sequences.

Transfection refers to the taking up of an expression vector by a host cell whether or not any coding sequence are in fact expressed. Numerous methods of transfection are known to the ordinarily skilled artisan, for example, the calcium phosphate precipitation method and electroporation are commonly used. Successful transfection is generally recognized when any indication of the operation of the vector occurs within the host cell.

Transformation means introducing DNA into an organism so that the DNA is replicable, either as an extrachromosomal element or by chromosomal integration. Depending on the host cell used, transformation is done using standard techniques appropriate to such cells. Transformations into yeast are typically carried out according to the method of Van Solingen et al., *J. Bact.*, 130, 946 (1977) and Hsiao et al., *Proc. Natl. Acad. Sci. (USA)*, 76(8)3829–3833 (1979). However, other methods for introducing DNA into cells such as by nuclear injection, electroporation, or protoplast fusion may also be used.

5. Cell Culture

Cells used to produce the αINT1 gene product are cultured in suitable media, as described generally in Sambrook et al. Commercially available media such as Hams F10 (Sigma), Minimal Essential Medium (MEM, Sigma), RPMI-1640 (Sigma), and Dulbecco's Modified Eagle's Medium (DMEM, Sigma) are suitable for culturing the host cells. These media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics (such as Gentamycin' drug), trace elements (defined as inorganic compounds usually present at final concentrations in the micromolar range), and glucose, galactose, or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan. Induction of cells, to cause expression of the protein, is accomplished using the procedures required by the particular expression system selected.

The invention has been described with reference to various specific and preferred embodiments and will be further described by reference to the following detailed examples. It is understood, however, that there are many extensions, variations and modifications on the basic theme of the present invention beyond that shown in the examples and detailed description, which are within the spirit and scope of the present invention.

EXAMPLES

Isolation of the Gene αINT1 from *Candida albicans*

DNA from spheroplasts of *C. albicans* 10261 (American Type Culture Collection) was isolated according to standard procedures as disclosed in Davis et al., *Methods Enzymol.*, 65 404–411 (1980), digested with the restriction enzyme Sau3AI, and packaged in λEMBL3 (Stratagene). Preliminary studies confirmed that a 3.5 kbp EcoRI fragment of *C. albicans* DNA hybridized with a 314 bp EcoRI/SmaI DNA fragment derived from the transmembrane domain of human αM as disclosed in Hickstein et al., *Proc. Natl. Acad. Sci. USA*, 86, 257–261, 1989. Primers for amplification of the EcoRI/SmaI αM DNA fragment were as follows: upstream primer: 5' GAATTCAATGCTACCCTCAA (SEQ ID NO:9); and downstream primer: 5° CCCGGGGGACCCCCTTCACT (SEQ ID NO:10).

A library enriched for 3.0–3.8 kbp EcoRI fragments from *C. albicans* was constructed by digestion of genomic DNA with EcoRI and ligation to pBluescript II SK(+). Plasmid minipreparations from a total of 200 colonies were screened by the sib selection technique for hybridization at 50° C. with [$^{32}$P]-labeled PCR product. Five clones were isolated from three successive screenings. Two of the five clones gave reproducible signals after hybridization with a degenerate oligonucleotide encoding a conserved sequence [KVGFFK] in the cytoplasmic domain of αX: 5' AA(AG) GT(CT) GG(AT) TT(CT) TT(CT) AA(AG) 3' (SEQ ID NO:11). Both clones contained a 3.5 kbp EcoRI insert and failed to hybridize with a degenerate oligonucleotide from the *S. cerevisiae* gene USO1:5' GAA AT(ACT) GA(CT) GA(CT) TT(AG) ATG 3' (SEQ ID NO: 12).

A 500 bp HindIII subfragment from one of these clones was used to screen 20,000 clones from a library of *C. albicans* 10261 genomic DNA (prepared commercially from *C. albicans* DNA by Stratagene) by the plaque hybridization technique as disclosed in Sambrook et al., *Molecular Cloning: A Laboratory Manual*, Cold Spring Harbor Lab. Press, Plainview, N.Y., 2nd Ed., pp.2.108–2.125 (1989). The largest hybridizing insert, a 10.5 kbp SalI fragment, was isolated by agarose gel electrophoresis, cloned, and sequenced.

Sequence Analysis

Both strands of the 10.5 kbp SalI fragment were sequenced by the method of gene walking on an Applied Biosystems Model 373 Automated Sequencer in the University of Minnesota Microchemical Facility. Nucleotide and protein sequence analyses were performed with the Genetics Computer Group (U. of WI, Madison) Sequence Analysis Software Package, version 7.0. The nucleotide sequence of the coding strand plus approximately 100 upstream nucleotides and 100 nucleotides of 3' untranslated sequence and the derived amino acid sequence (GenBank Acc. No. U35070) are shown in Tables 1 (SEQ ID NO:1) and 2 (SEQ ID NO:2), respectively. By Southern blot analysis under conditions of high stringency (hybridization at 65° C., final wash in 0.2× SSC/0.1% SDS at 65° C.), this gene is present only in *C. albicans* and not in strains of *C. tropicalis, C. krusei, C glabrata*, or *S. cerevisiae*.

TABLE 1

| | | | | | | |
|---|---|---|---|---|---|---|
| 1 | cccaaaaag | ataaataaa | aacaaaacaa | aacaaaagta | ctaacaaatt | attgaaactt |
| 61 | ttaattttta | ataagaatc | agtagatcta | ttgttaaaag | aaatgaactc | aactccaagt |
| 121 | aaattattac | cgatagataa | acattctcat | ttacaattac | agcctcaatc | gtcctcggca |
| 181 | tcaatattta | attcccaac | aaaaccattg | aatttccca | gaacaaattc | caagccgagt |
| 241 | ttagatccaa | attcaagctc | tgatacctac | actagcgaac | aagatcaaga | gaaagggaaa |
| 301 | gaagagaaaa | aggacacagc | ctttcaaaca | tcttttgata | gaaattttga | tcttgataat |
| 361 | tcaatcgata | tacaacaaac | aattcaacat | cagcaacaac | agccacaaca | acaacaacaa |
| 421 | ctctcacaaa | ccgacaataa | tttaattgat | gaattttctt | ttcaaacacc | gatgacttcg |
| 481 | actttagacc | taaccaagca | aaatccaact | gtggacaaag | tgaatgaaaa | tcatgcacca |
| 541 | acttatataa | atacctcccc | caacaaatca | ataatgaaaa | aggcaactcc | taaagcgtca |
| 601 | cctaaaaag | ttgcatttac | tgtaactaat | cccgaaattc | atcattatcc | agataatgaa |
| 661 | gtcgaggaag | aagatcaaag | tcaacaaaaa | gaagattcag | ttgagccacc | cttaatacaa |
| 721 | catcaatgga | aagatccttc | tcaattcaat | tattctgatg | aagatacaaa | tgcttcagtt |
| 781 | ccaccaacac | caccacttca | tacgacgaaa | cctacttttg | cgcaattatt | gaacaaaaac |
| 841 | aacgaagtca | atctggaacc | agaggcattg | acagatatga | aattaaagcg | cgaaaatttc |
| 901 | agcaatttat | cattagatga | aaaagtcaat | ttatatctta | gtcccactaa | taataacaat |
| 961 | agtaagaatg | tgtcagatat | ggatctgcat | ttacaaaact | tgcaagacgc | ttcgaaaaac |
| 1021 | aaaactaatg | aaaatattca | caattigtca | tttgctttaa | aagcaccaaa | gaatgatatt |
| 1081 | gaaaacccat | taaactcatt | gactaacgca | gatattctgt | taagatcatc | tggatcatca |
| 1141 | caatcgtcat | tacaatcttt | gaggaatgac | aatcgtgtct | tggaatcagt | gcctgggtca |
| 1201 | cctaagaagg | ttaatcctgg | attgtctttg | aatgacggca | taagggggtt | ctctgatgag |
| 1261 | gttgttgaat | cattacttcc | tcgtgactta | tctcgagaca | aattagagac | tacaaaagaa |
| 1321 | catgatgcac | cagaacacaa | caatgagaat | tttattgatg | ctaaatcgac | taataccaat |
| 1381 | aagggacaac | tcttagtatc | atctgatgat | catttggact | cttttgatag | atcctataac |
| 1441 | cacactgaac | aatcaatttt | gaatcttttg | aatagtgcat | cacaatctca | aatttcgtta |
| 1501 | aatgcattgg | aaaaacaaag | gcaaacacag | gaacaagaac | aaacacaagc | ggcagagcct |
| 1561 | gaagaagaaa | cttcgtttag | tgataatatc | aaagttaaac | aagagccaaa | gagcaatttg |
| 1621 | gagtttgtca | aggttaccat | caagaaagaa | ccagttctgg | ccacggaaat | aaaagctcca |
| 1681 | aaaagagaat | tttcaagtcg | aatattaaga | ataaaaaatg | aagatgaaat | tgccgaacca |
| 1741 | gctgatattc | atcctaaaaa | agaaaatgaa | gcaaacagtc | atgtcgaaga | tactgatgca |
| 1801 | ttgttgaaga | aagcacttaa | tgatgatgag | gaatctgaca | cgacccaaaa | ctcaacgaaa |
| 1861 | atgtcaattc | gttttcatat | tgatagtgat | tggaaattgg | aagacagtaa | tgatggcgat |
| 1921 | agagaagata | atgatgatat | ttctcgtttt | gagaaatcag | atatttgaa | cgacgtatca |
| 1981 | cagacttctg | atattattgg | tgacaaatat | ggaaactcat | caagtgaaat | aaccaccaaa |
| 2041 | acattagcac | ccccaagatc | ggacaacaat | gacaaggaga | attctaaatc | tttggaagat |
| 2101 | ccagctaata | atgaatcatt | gcaacaacaa | ttggaggtac | cgcatacaaa | agaagatgat |
| 2161 | agcattttag | ccaactcgtc | caatattgct | ccacctgaag | aattgacttt | gcccgtagtg |
| 2221 | gaagcaaatg | attattcatc | ttttaatgac | gtgaccaaaa | cttttgatgc | atactcaagc |
| 2281 | tttgaagagt | cattatctag | agagcacgaa | actgattcaa | aaccaattaa | tttcatatca |
| 2341 | atttggcata | aacaagaaaa | gcagaagaaa | catcaaattc | ataaagttcc | aactaaacag |
| 2401 | atcattgcta | gttatcaaca | atacaaaaac | gaacaagaat | ctcgtgttac | tagtgataaa |
| 2461 | gtgaaaatcc | caaatgccat | acaattcaag | aaattcaaag | aggtaaatgt | catgtcaaga |
| 2521 | agagttgtta | gtccagacat | ggatgattig | aatgtatctc | aatttttacc | agaattatct |
| 2581 | gaagactctg | gatttaaaga | tttgaatttt | gccaactact | ccaataacac | caacagacca |
| 2641 | agaagtttta | ctccattgag | cactaaaaat | gtcttgtcga | atattgataa | cgatcctaat |
| 2701 | gttgttgaac | ctcctgaacc | gaaatcatat | gctgaaatta | gaatgctag | acggttatca |
| 2761 | gctaataagg | cagcgccaaa | tcaggcacca | ccattgccac | cacaacgaca | accatcttca |
| 2821 | actcgttcca | attcaaataa | acgagtgtcc | agattagag | tgcccacatt | tgaaattaga |
| 2881 | agaactctt | cagcattagc | accttgtgac | atgtataatg | atatttga | tgatttcggt |
| 2941 | gcgggttcta | aaccaactat | aaaggcagaa | ggaatgaaaa | cattgccaag | tatggataaa |
| 3001 | gatgatgtca | agaggatttt | gaatgcaaag | aaaggtgtga | ctcaagatga | atatataaat |
| 3061 | gccaaacttg | ttgatcaaaa | acctaaaaag | aattcaattg | tcaccgatcc | cgaagaccga |
| 3121 | tatgaagaat | tacaacaaac | tgcctctata | cacaatgcca | ccattgattc | aagtatttat |
| 3181 | ggccgaccag | actccatttc | taccgacatg | ttgccttatc | ttagtgatga | attgaaaaaa |
| 3241 | ccacctacgg | ctttatattc | tgctgatcgt | ttgtttatgg | aacaagaagt | acatccgtta |
| 3301 | agatcaaact | ctgttttggt | tcacccaggg | gcaggagcag | caactaattc | ttcaatgtta |
| 3361 | ccagagccag | attttgaatt | aatcaattca | cctgctagaa | atgtgctgaa | caacagtgat |
| 3421 | aatgtcgcca | tcagtggtaa | tgctagtact | attagtttta | accaattgga | tatgaatttt |
| 3481 | gatgaccaag | ctacaattgg | tcaaaaatc | caagagcaac | ctgcttcaaa | atccgccaat |
| 3541 | actgttcgtg | gtgatgatga | tggattggcc | agtgcacctg | aaacaccaag | aactcctacc |
| 3601 | aaaaaggagt | ccatatcaag | caagcctgcc | aagctttctt | ctgcctcccc | tagaaaatca |
| 3661 | ccaattaaga | ttggttcacc | agttcgagtt | attaagaaaa | atggatcaat | tgctggcatt |
| 3721 | gaaccaatcc | caaaagccac | tcacaaaccg | aagaaatcat | tccaaggaaa | cgagatttca |
| 3781 | aaccataaag | tacgagatgg | tggaatttca | ccaagctccg | gatcagagca | tcaacagcat |
| 3641 | aatcctagta | tggtttctgt | tccttcacag | tatactgatg | ctacttcaac | ggttccagat |
| 3901 | gaaaacaaag | atgttcaaca | caagcctcgt | gaaaagcaaa | agcaaaagca | tcaccatcgc |
| 3961 | catcatcatc | atcatcaaa | acaaaaaact | gatattccgg | gtgttgttga | tgatgaaatt |
| 4021 | cctgatgtg | gattacaaga | acgaggcaaa | ttattcttta | gagttttagg | aattaagaat |
| 4081 | atcaatttac | ccgatattaa | tactcacaaa | ggaagattca | ctttaacgtt | ggataatgga |
| 4141 | gtgcattgtg | ttactacacc | agaatacaac | atggacgacc | ataatgttgc | cataggtaaa |
| 4201 | gaatttgagt | tgacagttgc | tgattcatta | gagtttattt | taactttgaa | ggcatcatat |
| 4261 | gaaaaacctc | gtgtgtacatt | agtagaagtg | actgaaaaga | aagttgtcaa | atcaagaaat |
| 4321 | agattgagtc | gattatttgg | atcgaaagat | attatcacca | cgacaaagtt | tgtgcccact |

TABLE 1-continued

| 4381 | gaagtcaaag | atacctgggc | taataagttt | gctcctgatg | gttcatttgc | tagatgttac |
|------|------------|------------|------------|------------|------------|------------|
| 4441 | attgatttac | aacaatttga | agaccaaatc | accggtaaag | catcacagtt | tgatctcaat |
| 4501 | tgtttaatg | aatgggaaac | tatgagtaat | ggcaatcaac | caatgaaaag | aggcaaacct |
| 4561 | tataagattg | ctcaattgga | agttaaaatg | ttgtatgttc | cacgatcaga | tccaagagaa |
| 4621 | atattaccaa | ccagcattag | atccgcatat | gaaagcatca | atgaattaaa | caatgaacag |
| 4681 | aataattact | ttgaaggtta | tttacatcaa | gaaggaggtg | attgtccaat | ttttaagaaa |
| 4741 | cgttttttca | aattaatggg | cacttcttta | ttggctcata | gtgaaatatc | tcataaaact |
| 4801 | agagccaaaa | ttaatttatc | aaaagttgtt | gatttgattt | atgttgataa | agaaaacatt |
| 4861 | gatcgttcca | atcatcgaaa | tttcagtgat | gtgttattgt | tggatcatgc | attcaaaatc |
| 4921 | aaatttgcta | atggtgagtt | gattgatttt | tgtgctccta | ataaacatga | aatgaaaata |
| 4981 | tggattcaaa | atttacaaga | aattatctat | agaaatcggt | tcagacgtca | accatgggta |
| 5041 | aatttgatgc | ttcaacaaca | acaacaacaa | caacaacaac | aaagctccca | acagtaattg |
| 5101 | aaaggtctac | ttttgatttt | tttaatttta | attggcaaat | atatgcccat | ttttgtattat |
| 5161 | cttttagtct | aatagcgttt | tctttttttc | cagt | | |

TABLE 2

```
   1 MNSTPSKLLPIDKHSHLQLQPQSSSASIFNSPTKPLNFPRTNSKPSLDPN
  51 SSSDTYTSEQDQEKGKEEKKDTAFQTSFDRNFDLDNSIDIQQTIQHQQQQ
 101 PQQQQQLSQTDNNLIDEFSFQTPMTSTLDLTKQNPTVDKVNENHAPTYIN
 151 TSPNKSIMKKATPKASPKKVAFTVTNPEIHHYPDNRVEEEDQSQQKEDSV
 201 EPPLIQHQWKDPSQFNYSDEDTNASVPPTPPLHTTKPTFAQLLNKNNEVN
 251 SEPEALTDMKLKRENFSNLSLDEKVNLYLSPTNNNNSKNVSDMDSHLQNL
 301 QDASKNKTNENIHNLSFALKAPKNDIENPLNSLTNADISLRSSGSSQSSL
 351 QSLRNDNRVLESVPGSPKKVNPGLSLNDGIKGFSDEVVESLLPRDLSRDK
 401 LETTKEHDAPEHNNENFIDAKSTNTNKGQLLVSSDDHLDSFDRSYNHTEQ
 451 SILNLLNSASQSQISLNALEKQRQTQEQEQTQAAEPEEETSFSDNIKVKQ
 501 EPKSNLEFVKVTIKKEPVSATEIKAPKREFSSRILRIKNEDEIAEPADIH
 551 PKKENEANSHVEDTDALLKKALNDDEESDTTQNSTKMSIRFHIDSDWKLE
 601 DSNDGDREDNDDISRFEKSDILNDVSQTSDIIGDKYGNSSSEITTKTLAP
 651 PRSDNNDKENSKSLEDPANNESLQQQLEVPHTKEDDSILANSSNIAPPEE
 701 LTLPVVEANDYSSFNDVTKTFDAYSSFEESLSREHETDSKPINFISIWHK
 751 QEKQKKHQIHKVPTKQIIASYQQYKNEQESRVTSDKVKIPNAIQFKKFKE
 801 VNVMSRRVVSPDMDDLNVSQFLPELSEDSGFKDLNFANYSNNTNRPRSFT
 851 PLSTKNVLSNIDNDPNVVEPPEPKSYAEIRNARRLSANKAAPNQAPPLPP
 901 QRQPSSTRSNSNKRVSRFRVPTFEIRRTSSALAPCDMYNDIFDDFGAGSK
 951 PTIKAEGMKTLPSMDKDDVKRILNAKKGVTQDEYINAKLVDQKPKKNSIV
1001 TDPEDRYEELQQTASIHNATIDSSIYGRPDSISTDMLPYLSDELKKPPTA
1051 LLSADRLFMEQEVHPLRSNSVLVHPGAGAATNSSMLPEPDFELINSPARN
1101 VSNNSDNVAISGNASTISFNQLDMNFDDQATIGQKIQEQPASKSANTVRG
1151 DDDGLASAPETPRTPTKKESISSKPAKLSSASPRKSPIKIGSPVRVIKKN
1201 GSIAGIEPIPKATHKPKKSFQGNEISNHKVRDGGISPSSGSEHQQHNPSM
1251 VSVPSQYTDATSTVPDENKDVQHKPREKQKQKHHHRHHHHHHKQKTDIPG
1301 VVDDEIPDVGLQERGKLFFRVLGIKNINLPDINTHKGRFTLTLDNGVHCV
1351 TTPEYNMDDHNVAIGKEFELTVADSLEFILTLKASYEKPRGTLVEVTEKK
1401 VVKSRNRLSRLFGSKDIITTTKFVPTEVKDTWANKFAPDGSFARCYIDLQ
1451 QFEDQITGKASQFDLNCFNEWETMSNGNQPMKRGKPYKIAQLEVKMLYVP
1501 RSDPREILPTSIRSAYESINELNNEQNNYFEGYLHQEGGDCPIFKKRFFK
1551 LMGTSLLAHSEISHKTRAKINLSKVVDLIYVDKENIDRSNHRNFSDVLLL
1601 DHAFKIKFANGELIDFCAPNKHEMKIWIQNLQEIIYRNRFRRQPWVNLML
1651 QQQQQQQQQQSSQQ
```

Functional Domains

A 236 amino acid sequence near the amino terminus of the gene product (αInt1p) is shown in Table 3 (SEQ ID NO:3). This sequence, or a portion thereof, is believed to encompass the ligand binding site, or a portion thereof, and would provide very useful antibodies or could be used as a vaccine antigen itself.

TABLE 3

```
              SDEDTNASVPPTPPLHTTKPTFAQLLNKNEVN
251 SEPEALTDMKLKRENFSNLSLDEKVNLYLSPTNNNNSKNVSDMDSHLQNL
301 QDASKNKTNENIHNLSFALKAPKNDIENPLNSLTNADISLRSSGSSQSSL
351 QSLRNDNRVLESVPGSPKKVNPGLSLNDGIKGFSDEVVESLLPRDLSRDK
401 LETTKEHDAPEHNNENFIDAKSTNTNKGQLLVSSDDHLDSFDRSYNHTEQ
451 SIL
```

The following peptide sequences were used as antigens for the preparation of anti-peptide polyclonal antibodies in rabbits by commercial contract through Cocalico Biologicals (Reamstown, Pa.). The sequences B-F are listed below and correspond to the protein sequence of αInt1p as reported in GenBank, with the exception of one amino acid substitution in sequence (B), as noted below.

B. A 23-mer peptide encompassing the first cation-binding site. This peptide was synthesized by BioSynthesis Inc. (Lewisville, Tex.). Note that the peptide sequence is MDL, while the GenBank sequence is MDS.

YLS PTN NNN SKN VSD MDL HLQ NL (SEQ ID NO:4)

C. A 23-mer peptide encompassing the second divalent cation-binding site. This peptide was synthesized by Bio-Synthesis Inc. (Lewisville, Tex.).

DWK LED SND GDR EDN DDI SRF EK (SEQ ID NO:5)

D. A 17-mer peptide spanning the RGD site and flanking residues. This peptide was synthesized by the Microchemical Facility of the University of Minnesota.

SKS ANT VRG DDD GLA SA (SEQ ID NO: 6)

E. A 17-mer peptide from the MIDAS motif of αInt1p. This peptide was synthesized by the Microchemical Facility of the University of Minnesota.

DHL DSF DRS YNH TEQ SI (SEQ ID NO:7)

F. A 17-mer peptide from the C-terminus of αInt1p. This peptide was synthesized by the Microchemical Facility of the University of Minnesota.

WIQ NLQ EII YRN RFR RQ (SEQ ID NO:8)

Preparation and Evaluation of Antibodies

Polyclonal antibodies were prepared by Cocalico Biologics (Reamstown, Pa.) using the peptides B–F (SEQ ID NOS:4–8) listed above. Generally, each peptide is coupled to an adjuvant, the peptide-adjuvant mixture is injected into rabbits, and the rabbit receives booster injections of the same mixture every three-four weeks. Rabbit serum is withdrawn three weeks after the injections and tested for its titer against the original peptide.

Figure 2:
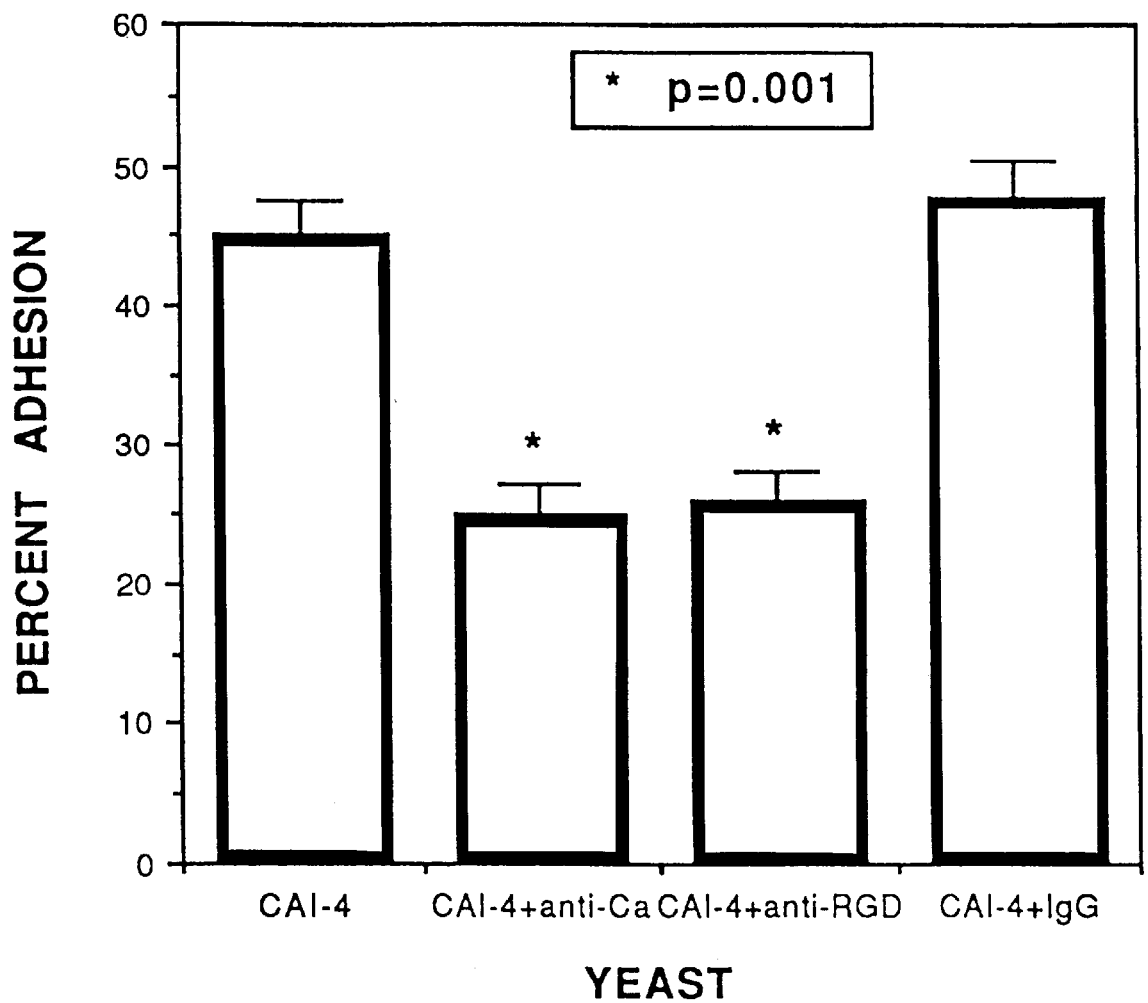
FIG. 2 is a graph of the blockade of candidal adhesion to CHO cells by antibodies to αIntp1.

One rabbit each was used to raise antibodies to each individual peptide. IgG antibodies were purified from the respective rabbit's antiserum by affinity purification on a Protein A-Sepharose column (BioRad) according to standard methods. In FIGS. 1 and 2, anti-Ca denotes antibodies raised to the 23-mer peptide (SEQ ID NO:5) encompassing the second divalent cation binding site; anti-RGD denotes antibodies to the 17-mer peptide encompassing the RGD site and flanking residues (SEQ ID NO:6). CAI-4 denotes the strain of *C. albicans* that was employed. Anti-Ca or anti-RGD antibodies in a concentration of 1.0 mg/ml were incubated with $1 \times 10^6 [^{35}S]$-methionine-labeled *C. albicans* blastospores for 30 minutes on ice at 4° C. Antibody-coated *C. albicans* blastospores were then incubated with confluent monolayers of HeLa cells in a 24-well microtiter plate for 60 minutes at 37° C. in 5% $CO_2$, as described in a previous publication (Bendel and Hostetter, *Journal of Clinical Investigation*, 92, 1840–1849 (1993)). Removal of non-adherent *C. alibicans* blastospores, release of the HeLa monolayer with attached *C. albicans* blastospores, counting of the radiolabel, calculation of specific adhesion, and controls for non-specific adhesion were all performed according to the methods in the publication cited above. For FIG. 2, methods remained the same, save that CHO cell monolayers (Chinese hamster ovary cells, a second epithelial cell line) were substituted for HeLa cell monolayers.

FIG. 1 shows that the antibodies against the second divalent cation binding site (SEQ ID NO:5) or the RGD site and flanking residues (SEQ ID NO:6) inhibit binding to HeLa cells by about 50%. FIG. 2 shows that antibodies against the second divalent cation binding site or the RGD site inhibit binding to CHO cells by about 50%.

Induction of αInt1p-Dependent Germ Tubes in *Saccharomyces cerevisiae*

The entire open reading frame of αINT1 (BglII/SalI fragment) was subcloned into the plasmid pBM272 (obtained from Dr. James Bodley, University of Minnesota) after digestion with BamHI and SalI, in order to place the GAL1-10 promoter upstream of the αINT1 start codon. This plasmid was named pCG01. *S. cerevisiae* YPH500, obtained from the Yeast Genetic Stock Center (Berkeley, Calif.), was transformed with pBM272 or pCG01 by the lithium acetate procedure as disclosed in Ito et al., *J. Bacteriol.*, 153(1), 163–168 (1983). Transformants were selected on agar-based minimal medium (MM=0.17% yeast nitrogen base/0.5% ammonium sulfate) with 2% glucose, in the absence of uracil. Induction of αINT1 was achieved by growing transformants containing pCG01 to mid-exponential phase in non-inducing, non-repressing medium (MM without uracil with 2% raffinose) at 30° C., then harvesting, washing, and resuspending them in inducing medium (MM without uracil with 2% galactose) at 30° C. for the expression of αINT1. YPH500 and YPH500 transformed with vector alone (pBM272) were grown under the identical conditions. *S. cerevisiae* transformants expressing αInt1p from the plasmid pCG 01 made abundant germ tubes after 6 hours' growth in inducing medium.

It will be appreciated by those skilled in the art that various modifications can be made to the above described embodiments of the invention without departing from the essential nature thereof. The invention is intended to encompass all such modifications within the scope of the appended claims. All publications, patents, and patent documents are incorporated by reference herein, as though individually incorporated by reference.

What is claimed is:

1. An isolated and purified peptide having an amino acid sequence selected from the group consisting of:
   (a) YLS PTN NNN SKN VSD MDL HLQ NL (SEQ ID NO:4);
   (b) DWK LED SND GDR EDN DDI SRF EK (SEQ ID NO:5);
   (c) SKS ANT VRG DDD GLA SA (SEQ ID NO:6);
   (d) DHL DSF DRS YNH TEQ SI (SEQ ID NO:7);
   (e) WIQ NLQ EII YRN RFR RQ (SEQ ID NO:8) and (f) SDE DTN ASV PPT PPL HTT KPT FAQ LLN KNN EVN SEP EAL TDM KLK REN FSN LSL DEK VNL YLS PTN NNN SKN VSD MDS HLQ NLQ DAS KNK TNE NIH NLS FAL KAP KND IEN PLN SLT NAD ISL RSS GSS QSS LQS LRN DNR VLE SVP GSP KKV NPG LSL NDG IKG FSD EVV ESL LPR DLS RDK LET TKE HDA PEH NNE NFI DAK STN TNK GQL LVS SDD HLD SFD RSY NHT EQS IL (SEQ ID NO:3).

2. An isolated and purified peptide, which has an amino acid sequence having SEQ ID NO:3.

3. The peptide of claims 1 or 2 wherein the peptide is immunogenic.

4. A composition for stimulating an immune response to a *Candida albicans*-derived integrin-like protein or peptide, wherein the composition comprises at least one peptide comprising an amino acid sequence selected from the group consisting of, SEQ ID NO:3, SEQ ID NO:4, SEQ ID NO:5, SEQ ID NO:6, SEQ ID NO:7, and SEQ ID NO:8, and a suitable adjuvant.

5. An immunogenic composition comprising one or more peptides selected from the group consisting of, SEQ ID NO:3, SEQ ID NO:4, SEQ ID NO:5, SEQ ID NO:6, SEQ ID NO:7, and SEQ ID NO:8, and a suitable adjuvant.

* * * * *

UNITED STATES PATENT AND TRADEMARK OFFICE
CERTIFICATE OF CORRECTION

PATENT NO. : 5,886,151
DATED : March 23, 1999
INVENTOR(S) : Hostetter et al.

It is certified that error appears in the above-identified patent and that said Letters Patent is hereby corrected as shown below:

Title page,
Item [21], Appl. No., delete "642,846" and replace with -- 08/642,846 --.
Item [56], References Cited, after "5,332,660 7/1994 Takeda et al. 435/6" insert
-- OTHER PUBLICATIONS -- and below it insert the following citations:

-- S. Alaei et al., "Isolation and Biochemical Characterization of the iC3b Receptor of *Candida albicans*," Inf. Immun., 61(4):1395-1399 (1993). --

-- C.M. Bendel et al., "Distinct Mechanisms of Epithelial Adhesion for *Candida albicans and Candida tropicalis*," J. Clin. Invest., 92, 1840-1849 (1993). --

-- C.M. Bendel et al., "Epithelial Adhesion in Yeast Species: Correlation with Surface Expression of the Integrin Analog, " J. Infec. Dis., 171, 1660-1663 (1995). --

-- R.A. Calderone et al., "Identification of C3d Receptors on *Candida albicans*," Infect. Immun., 56(1):252-258 (1988). --

-- R.A. Calderone, "Molecular Interactions at the Interface of *Candida albicans* and Host Cells," Arch. Of Med. Res., 24(3):275-279 (1993). --

-- R.A. Calderone, "Recognition between *Candida albicans* and host cells," Trends Microbiol., 1, 55-58 (1993). --

-- R.W. Davis et al., "Rapid DNA Isolations for Enzymatic and Hybridization Analysis," Methods Enzymol., 65, 404-411 (1980).--

-- Frey et al., "Localization and Distribution of IC3B Binding Sites on *Candida albicans*," 88th Annual Meeting of the American Society for Microbiology, Miami Beach, FL. May 8-13, 1988, Abstract No. F-29. --

-- C.A. Gale et al., "*A Candida Albicans* Gene with Integrin Motifs Induces Hyphal-Like Structures in S. Cerevisiae," Pediatric Res., 37(4), Part II, Abstract No. 1030, and poster presentation (1995). --

-- C. Gale et al., "Cloning and expression of a gene encoding an integrin-like protein in *Candida albicans*," Proc. Natl. Acad. Sci. USA, 93, 357-361 (1996). --

-- C.A.Gale et al., "Monoallelic Disruption of αINT1 Reduces AntibodyBinding, Adhesion, and Germ Tube Formation In *C. Albicans*," Pediatric Res., 37(4), Part II, Abstract No. 1014 (1995). --

UNITED STATES PATENT AND TRADEMARK OFFICE
CERTIFICATE OF CORRECTION

PATENT NO.   : 5,886,151
DATED        : March 23, 1999
INVENTOR(S)  : Hostetter et al.

It is certified that error appears in the above-identified patent and that said Letters Patent is hereby corrected as shown below:

-- B.J. Gilmore et al., "An iC3b Receptor on *Candida albicans:* Structure, Function, and Correlates for Pathogenicity, " J. Infect. Dis., 157(1), 38-46(1988). --

-- J.W. Goodman, "Immunogenicity & antigenic specificity," Basic and Clinical Immunology, Stites et al., eds., Appleton & Lange, Norwalk, CT, pp.101 and 108 (1991). --

-- K.S. Gustafson et al., "Molecular Mimicry in *Candida albicans,*" J.Clin. Invest., 87, 1896-1902 (1991). --

-- F. Heidenreich et al., "*Candida albicans* and *Candida stellatoidea*, in Contrast to Other *Candida* Species, Bind iC3b and C3d but Not C3b," Infect. Immun., 50(2), 598-600 (1985). --

-- D.D. Hickstein et al., "cDNA sequence for the αM subunit of the human neutrophil adherence receptor indicates homology to integrin α subunits," Proc. Natl. Acad. Sci. USA, 86, 257-261 (1989). --

-- M.K. Hostetter et al., Abstract of NIH Grant R-01 AI25827, funded 12/01/90 through 11/30/96. --

-- M.K. Hostetter, "A *Candida albicans* protein shares structural and functional properties with mammalian integrins," J. Cell Biol., Suppl. 0, 14 part A:164, Abst. No. 216 (1990). --

-- M.K. Hostetter, "Adhesion and Morphogenesis in Candida albicans," Pediatric Res., 39(4), 569-573 (1996). --

-- M.K: Hostetter et al., "The iC3b Receptor on *Candida albicans:* Subcellular Localization and Modulation of Receptor Expression by Glucose," J. Infect. Dis., -- M.K. Hostetter et al., "Adhesins and Ligands Involved in the Interaction Candida spp. with Epithelial and Endothelial Surfaces," Clinical Microbiology Reviews, 7(1):29-42 (1994). --

-- C. Hsiao et al., "High-frequency transformation of yeast by plasmids containing the cloned yeast ARG4 gene," Proc. Natl. Acad. Sci. USA, 76(8):3829-3833 (1979). --

-- R. Hurley, "Candidal Vaginitis," Proc. R. Soc. Med., 70(4):1-10 (1970). --

-- H. Ito et al., "Transformation of Intact Yeast Cells Treated with Alkali Cations,"J.

UNITED STATES PATENT AND TRADEMARK OFFICE
CERTIFICATE OF CORRECTION

PATENT NO.  : 5,886,151
DATED       : March 23, 1999
INVENTOR(S) : Hostetter et al.

It is certified that error appears in the above-identified patent and that said Letters Patent is hereby corrected as shown below:

-- E. Jakab et al., "Expression of vitronectin and fibronectin binding by *Candida albicans* yeast cells," APMIS, 101, 187-193 (1993). --

-- E.W. Jones, "Proteinase Mutants of Saccharomyces Cerevisiae," Genetics, 85(1):23-32 (1977). --

-- A.J. Kingsman et al., "Replication in *Saccharomyces cerevisiae* of Plasmid pBR313 Carrying DNA From the Yeat
 Region," Gene, 7, 141-152 (1979). --

-- S.A. Klotz et al., "Adherence of *Candida albicans* to immobilized extracellular matrix proteins is mediated by calcium dependent surface glycoproteins," Microbial Pathogenesis, 14,133-147 (1993). --

-- S.A. Klotz, "Plasma and Extracellular Matrix Proteins Mediate in the Fate of *Candida albicans* in the Human Host," Medical Hypotheses, 42, 328-334 (1994). --

-- Meinke et al., "Cloning of *C. albicans* DNA encoding an integrin analog, Pediatric Res., 35(4, part 2):187A, Abstract No. 1106 (1994). --

-- M. Michshita et al., "A Novel Divalent Cation-Binding Site in the A Domain of the $\beta 2$
Integin CR3 (CD11b/CD18) Is Essential for Ligand Binding," Cell, 72, 857-867 (1993). --

-- E. Negre et al., "The Collagen Binding Domain of Fibronectin Contains a High Affinity Binding Site for *Candida albicans,*" J. Biol. Chem., 269(35):22039-22045 (1994). --

-- Pollonelli et al., "New strategies in vaccination against fungal infections," J. Med. Vet. Mycology, 32(1):105-112 (1994). --

-- J. Sambrook et al., "Molecular Cloning: A Laboratory Manual," Cold Spring Harbor Laboratory Press, 108-125 (1989). --

-- G. Santoni et al., "Candida albicans expresses a fibronectin receptor antigenically related to $\alpha 5\beta 1$ integrin," Microbiology, 140, 2971-2979 (1994). --

-- D.T. Stinchcomb et al., "Isolation and characterisation of a yeast chromosomal replicator," Nature, 282, 39-43 (1979). --

UNITED STATES PATENT AND TRADEMARK OFFICE
CERTIFICATE OF CORRECTION

PATENT NO. : 5,886,151
DATED : March 23, 1999
INVENTOR(S) : Hostetter et al.

It is certified that error appears in the above-identified patent and that said Letters Patent is hereby corrected as shown below:

-- G. Tronchin et al., "Fungal Cell Adhesion Molecules in *Candida Albicans*," Eur. J. Epidemiol., 7(1):23-33 (1991). --
-- G. Tschumper et al., "Sequence of a yeast DNA fragment containing a chromosomal replicator and the TRP1 gene," Gene, 10, 157-166 (1980). --
-- P. Van Solingen et al., "Fusion of Yeast Spheroplasts," J. Bact., 130(2):946-947 (1977). --
-- T.C. White, "The Itegrin β1 Subunit form the Yeast, *Candida Albicans*," J. Cell Biochem. Suppl., [Abstract A243] 173 (1990). --

Column 12,
TABLE 1, in the left margin of the sequence listing, delete "3641" and replace with -- 3841 --.

Signed and Sealed this

Eleventh Day of December, 2001

*Attest:*

*Attesting Officer*

NICHOLAS P. GODICI
*Acting Director of the United States Patent and Trademark Office*